United States Patent [19]

Koizumi et al.

[11] Patent Number: 5,472,962
[45] Date of Patent: Dec. 5, 1995

[54] BENZOTHIOPHENE DERIVATIVE

[75] Inventors: Naoyuki Koizumi, Sagamihara; Shigehiro Takegawa; Shigeki Iwashita, both of Kawasaki; Tomoko Kawachi, Inagi; Teruaki Matsui, Kawasaki; Mamoru Mieda, Ebina; Hiroo Takahashi, Sagamihara; Tomoyuki Saito, Kawasaki; Kenyu Shibata, Inagi, all of Japan

[73] Assignee: Teikoku Hormone Mfg. Co., Ltd., Japan

[21] Appl. No.: 244,049

[22] PCT Filed: Nov. 11, 1992

[86] PCT No.: PCT/JP92/01465

§ 371 Date: May 13, 1994

§ 102(e) Date: May 13, 1994

[87] PCT Pub. No.: WO93/10113

PCT Pub. Date: May 27, 1993

[30] Foreign Application Priority Data

Nov. 15, 1991 [JP] Japan .................................... 3-326666

[51] Int. Cl.$^6$ ...................... A61K 31/38; A61K 31/445; C07D 409/10; C07D 333/64
[52] U.S. Cl. ...................... 514/233.5; 514/253; 514/307; 514/324; 514/422; 514/443; 514/444; 544/146; 544/376; 546/148; 546/202; 546/237; 548/525; 548/527; 549/51
[58] Field of Search .................... 544/146, 376; 546/148, 202, 237; 548/525, 527; 549/51; 514/233.5, 25.3, 307, 324, 422, 443, 444

[56] References Cited

U.S. PATENT DOCUMENTS 4,007,204  2/1977  Descamps et al. ................... 260/330.5
4,156,732  5/1979  Lang et al. ............................. 549/51

FOREIGN PATENT DOCUMENTS 165810A  10/1985  European Pat. Off. .
52-53851  4/1977  Japan .
57-181081  8/1982  Japan .
57-181079  8/1982  Japan .
1013907  12/1965  United Kingdom .

OTHER PUBLICATIONS

Gubin et al., European Journal of Medicinal Chemistry—Chimica Therapeurica, 10(4), pp. 418–424 (1975).
Duncan et al., Proc. Soc. Exp. Biol. Med. 112, 439–442 (1963).
Lednicer et al., J. Med. Chem. 8, 725–726 (1965).
Jones et al., J. Med. Chem. 22, 962–966 (1979).
Black et al., Life Sci. 26, 1453–1458 (1980).
E. Campaigne et al., *Journal of Organic Chemistry*, vol. 26, No. 1, pp. 363–365 (1961).

*Primary Examiner*—C. Warren Ivy
*Assistant Examiner*—Ba K. Trinh
*Attorney, Agent, or Firm*—Wenderoth, Lind & Ponack

[57] ABSTRACT

A benzothiophene derivative represented by the formula

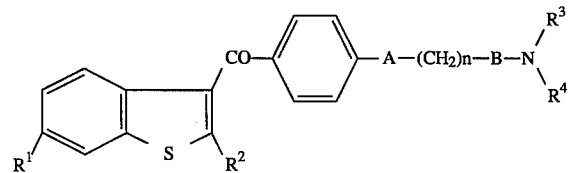

or a salt thereof has an excellent antiestrogenic activity, and is useful as a therapeutic agent of breast cancer, endometrial cancer, endometriosis, mastopathy, etc.

This compound is characterized in that the 2-position (the substituent $R^2$) of the benzothiophene nucleus is substituted by a halogen atom; a lower alkyl group; or a cycloalkyl or cycloalkenyl group optionally substituted by a lower alkyl group, a hydroxyl group, acyloxy group or an oxo group.

11 Claims, No Drawings

BENZOTHIOPHENE DERIVATIVE

TECHNICAL FIELD

This invention relates to novel benzothiophene derivatives having an antiestrogenic activity, and relates more detailedly to benzothiophene derivatives represented by the formula

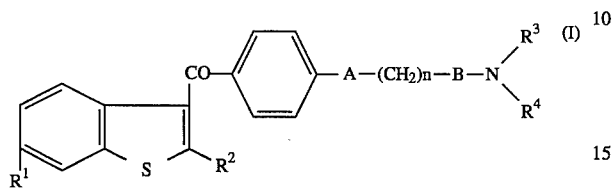

wherein, $R^1$ denotes a hydrogen atom, a hydroxyl group, a lower alkoxy group, an acyloxy group or an N,N-di-lower alkyl-substituted or unsubstituted carbamoyloxy group, $R^2$ denotes a halogen atom; a lower alkyl group; or a cycloalkyl or cycloalkenyl group optionally substituted by a lower alkyl group, a hydroxyl group, an acyloxy group or an oxo group, $R^3$ and $R^4$ each denote a hydrogen atom or a lower alkyl group, or $R^3$ and $R^4$ combine with the nitrogen atom to which they bind, to denote a heterocyclic ring which may further contain a hetero atom selected from O, S and N, A denotes O or $CH_2$, B denotes C=O or $CH_2$, and n denotes 1 or 2.

BACKGROUND ART

In gynecologic cancers such as breast cancer and endometrial cancer, the activities of the estrogen receptor and the estrogen-biosynthesizing enzyme in the tumor tissue are higher than those in the normal mammary gland tissue and the endometrial tissue, and the proliferation of these tumors have close relation to endogenous or local increase of estrogenic activity. Thus as one means for therapy of gynecologic cancers, it is put into practice to make competition against the estrogenic effect in the estrogenic target tissue, namely to administer antiestrogenic agents.

Among these antiestrogenic agents, a compound of the following formula called tamoxifen was, first, proposed (see, UK Patent No. 1,013,907).

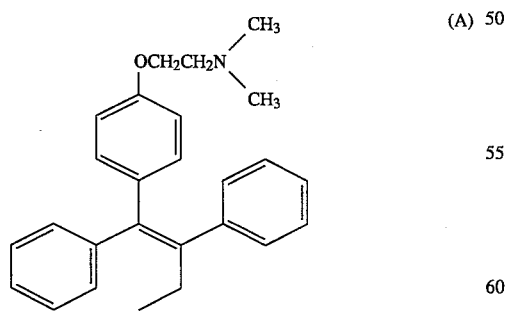

Tamoxifen is now widely used for treatment of breast cancer, etc. as a representative antiestrogenic agent. Thereafter, several kinds of compounds having the same characteristic as tamoxifen is chemical structure, namely three benzene rings were proposed as antiestrogenic agents (see, for example, Proc. Soc. Exp. Biol. Med., 112, 439–442 (1963), J. Med. Chem. 8, 725–726 (1965), J. Med. Chem., 22, 962–966 (1979)).

Further, several benzothiophene derivatives having an antiestrogenic activity have been known (see, Japanese Laid-Open Patent Publication No. 181081/1982, Life Sci., 26, 1453–1458, 1980). Among them, a compound of the following formula called raloxifene has a very strong antiestrogenic activity, and is now under clinical tests.

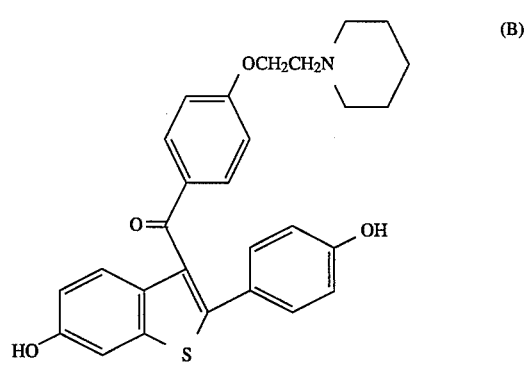

However, all of these antiestrogenic agents also have an estrogenic activity too strong to be neglected, simultaneously with the antiestrogenic activity, and they were yet unsatisfactory in this point.

The present inventors have intensely researched for benzothiophene derivatives having an antiestrogenic activity, and as a result have found that a series of compounds wherein a specific substituent such as a cycloalkyl group or a lower alkyl group was introduced in place of a substituted phenyl group so far known as the substituent as the 2-position of the benzothiophene nucleus have a strong antiestrogenic activity but have only a very weak estrogenic activity.

DISCLOSURE OF INVENTION

The term "lower" in this description means that the carbon atom number of a group or compound to which this term was attached is 6 or less, preferably 4 or less.

In the above formula (I), the "lower alkyl group" can be straight-chain or branched chain, and there can, for example, be mentioned a methyl, ethyl, n-propyl, isopropyl, n-butyl, sec-butyl, tert-butyl, n-pentyl or n-hexyl group or the like, and as the "lower alkoxy group", there can, for example, be mentioned a methoxy, ethoxy, n-propoxy, isopropoxy or n-butoxy group or the like. Further, as the "cycloalkyl group", those having 3 to 12 preferably 3 to 8 carbon atoms are preferable, and there can, for example, be mentioned a cyclopropyl, cyclobutyl, cyclopentyl, cyclohexyl, cycloheptyl or cyclooctyl group or the like, and as the "cycloalkenyl group", those having 4 to 12, preferably 5 to 8 carbon atoms are preferable, and there can, for example, be mentioned a 1-cyclopentenyl, 1-cyclohexenyl, 1-cycloheptenyl or 1-cyclooctenyl group or the like. Further, the "halogen atom" includes a fluorine, chlorine, or bromine atom.

The "acyloxy group" is specifically a group represented by the formula $R^7CO-O-$ or $R^8SO_2-O-$, and therein $R^7$ denotes a hydrogen atom; a lower alkyl group optionally substituted by a halogen atom, an amino group, a carbonyl group, a lower alkoxycarbonyl group, a lower alkanoyloxy group, a carbamoyl group or an aryl group; a lower alkenyl group optionally substituted by an aryl group; a lower cycloalkyl group; or an aryl group optionally substituted by a lower alkyl group, a lower alkoxy group or a halogen atom, or the like, $R^8$ denotes an aryl group optionally substituted by a lower alkyl group, or the like.

As examples of the "acyloxy group", there can be mentioned acetoxy, propionyloxy, trifluoroacetyloxy, glycyloxy, 3-carboxypropionyloxy, 3-ethoxycarbonylpropionyloxy, acetoxyacetoxy, phenylacetoxy, acryloyloxy, cyclohexanecarbonyloxy, benzoyloxy, 4-methoxybenzoyloxy, 2-chlorobenzoyloxy, methanesulfonyloxy and p-toluenesulfonyloxy groups, etc.

Further, when $R^2$ denotes "a cycloalkyl or cycloalkenyl group optionally substituted by a lower alkyl group, a hydroxyl group, an acyloxy group or an oxo group", the cycloalkyl or cycloalkenyl group can be a cycloalkyl or cycloalkenyl group unsubstituted or substituted by one lower alkyl, hydroxyl, acyloxy or oxo group, and therein, as the substituted cycloalkyl or cycloalkenyl group, there can, for example, be mentioned a 3-methylcyclopentyl, 3-hydroxycyclopentyl, 2-methylcyclohexyl, 3-methylcyclohexyl, 4-methylcyclohexyl, 4-hydroxycyclohexyl, 4-acetoxycyclohexyl, 4-benzoyloxycyclohexyl, 4-oxocyclohexyl or 2-methylcycloheptyl group or the like.

When, in the above formula (I), $R^3$ and $R^4$ "combine with the nitrogen atom to which they bind, to denote a heterocyclic ring which may further contain a hetero atom selected from O, S and N", the heterocyclic group may be substituted by a lower alkyl group or a hydroxyl group, or may be a condensed ring with a benzene ring. Further, in the heterocyclic group, the nitrogen atom-containing ring is preferably a 5- to 7-membered heterocyclic ring.

Thus, as examples of the group

there can be mentioned amino, methylamino, isopropylamino, dimethylamino, diethylamino, pyrrolidinyl, piperidinyl, homopiperidinyl, piperazinyl, morpholinyl, thiomorpholinyl, 3-methylpyrrolidinyl, 3-methylpiperidinyl, 4-hydroxypiperidinyl, 4-methylpiperazinyl, 4-ethylpiperazinyl, 2,3-dihydroindolyl or 1,2,3,4-tetrahydroisoquinolyl group or the like.

A preferred group of compounds among the compounds of the above formula (I) are compounds of the formula (I) wherein $R^1$ denotes a hydroxyl group. Further, another preferred group of compounds are compounds of the formula (I) wherein $R^2$ denotes a branched chain lower alkyl group, particularly a group of the formula

(wherein $R^5$ and $R^6$ each denote a lower alkyl group), or a cycloalkyl group having 3 to 8 carbon atoms optionally substituted by a lower alkyl group or a hydroxyl group.

As specific examples of the compounds of the above formula (I) provided by this invention, the following ones can be mentioned besides those set forth in the later-described examples.

(6-hydroxy-2-cyclopentylbenzo[b]thien-3-yl)[4-[2-[1-(4-methylpiperazinyl)]ethoxy] phenyl]methanone, (6-hydroxy-2-cyclohexylbenzo[b]thien-3-yl)[4-[2-[1-(3-methylpyrrolidinyl)]ethoxy] phenyl]methanone, (6-hydroxy-2-cyclohexylbenzo[b]thien-3-yl)[4-[2-(N-thiomorpholinyl)-ethoxy]phenyl]methanone, (6-methanesulfonyloxy-2-cyclohexylbenzo[b]-thien-3-yl)[4-[2-(1-piperidinyl)ethoxy]phenyl] methanone, (6-hydroxy-2-cycloheptylbenzo[b]thien-3-yl)[4-[2-(N-morpholinyl)ethoxy]phenyl]methanone, (6-hydroxy-2-cyclooctylbenzo[b]thien-3-yl)[4-[2-(1-piperidinyl)ethoxy]phenyl]methanone, (6-hydroxy-2-cyclododecylbenzo[b]thien-3-yl)[4-[2-(1-pyrrolidinyl)ethoxy]phenyl]methanone,

[6-hydroxy-2-(2-methylcyclohexyl)benzo[b]thien-3-yl] [4-[2-(dimethylamino)ethoxy]phenyl] methanone,

[6-hydroxy-2-(4-hydroxycyclohexyl)benzo[b]-thien-3-yl][4-[2-(1-pyrrolidinyl)ethoxy] phenyl]methanone,

[6-hydroxy-2-(4-hydroxycyclohexyl)benzo[b]-thien-3-yl][4-[2-(1-homopiperidinyl)ethoxy]phenyl]methanone, (6-hydroxy-2-isopropylbenzo[b]thien-3-yl)[4-[2-(diethylamino)ethoxy]phenyl]methanone, (6-hydroxy-2-isopropylbenzo[b]thien-3-yl)[4-[2-(1-homopiperidinyl)ethoxy]phenyl]methanone, (6-hydroxy-2-sec-butylbenzo[b]thien-3-yl)[4-[2-(1-piperidinyl)ethoxy]phenyl]methanone, (6-hydroxy-2-cyclohexylbenzo[b]thien-3-yl)[4-[3-(dimethylamino)propoxy]phenyl]methanone,

[6-hydroxy-2-(3-methylcyclohexyl)benzo[b]thien-3-yl] [4-[3-(1-piperidinyl)propoxy] phenyl]methanone, (6-hydroxy-2-isopropylbenzo[b]thien-3-yl)[4-[3-(1-piperidinyl)propoxy]phenyl]methanone, (6-hydroxy-2-cyclohexylbenzo[b]thien-3-yl)[4-[2-(diethylcarbamoyl)ethyl]phenyl]methanone,

[6-hydroxy-2-(3-methylcyclohexyl)benzo[b]thien-3-yl] [4-[2-(1-piperidinylcarbonyl)ethyl]phenyl]methanone, (6-hydroxy-2-isopropylbenzo[b]thien-3-yl)[4-[2-(1-piperidinylcarbonyl)ethyl]phenyl] methanone, (6-hydroxy-2-cyclohexylbenzo[b]thien-3-yl)[4-[3-(1-homopiperidinyl)propyl]phenyl] methanone, (6-hydroxy-2-cyclohexylbenzo[b]thien-3-yl)[4-[3-(N-morpholinyl)propyl]phenyl]methanone, (6-hydroxy-2-isopropylbenzo[b]thien-3-yl)[4-[3-(1-pyrrolidinyl)propyl]phenyl] methanone, (6-hydroxy-2-cyclopentylbenzo[b]thien-3-yl)[4-[3-(1-pyrrolidinylcarbonyl)propyl]phenyl] methanone,

[6-hydroxy-2-(2-methylcyclohexyl)benzo[b]thien-3-yl] [4-[3-(1-piperidinylcarbonyl)propyl]phenyl]methanone, (6-hydroxy-2-cyclopentylbenzo[b]thien-3-yl)[4-[4-(1-piperidinyl)butyl]phenyl]methanone, (6-hydroxy-2-isopropylbenzo[b]thien-3-yl)[4-[4-(1-pyrrolidinyl )butyl]phenyl]methanone.

According to this invention, the compounds of the above formula (I) wherein B denotes $CH_2$ can be converted to salts. As examples of such salts, there can be mentioned acid addition salts with inorganic acids such as hydrochloric acid, hydrobromic acid, sulfuric acid, nitric acid and phosphoric acid; or organic acids such as acetic acid, propionic acid, succinic acid, maleic acid, benzoic acid, lactic acid, tartaric acid, citric acid and methanesulfonic acid, and among them, pharmacologically acceptable salts are preferable.

According to this invention, a compound of the above formula (I) or a salt thereof can, for example, be prepared by either (a) reacting a compound of the formula

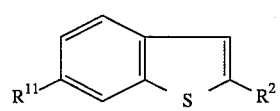

(II)

wherein $R^{11}$ denotes a hydrogen atom or a lower alkoxy group, and $R^2$ has the same meaning as above, with a compound of the formula

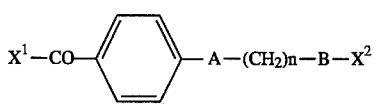   (III)

wherein $X^1$ and $X^2$ each denote a halogen atom, and A, B and n have the same meanings as above, and then reacting the resultant compound of the formula

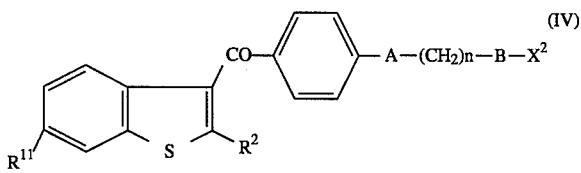   (IV)

wherein $R^{11}$, $R^2$, A, B, $X^2$ and n have the same meaning as above, with an amine of the formula

   (V)

wherein $R^3$ and $R^4$ have the same meanings as above, or (b) reacting a compound of the above formula (II) with a compound of the formula

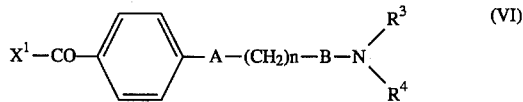   (VI)

wherein $R^3$, $R^4$, A, B, $X^1$ and n have the same meanings as above, and then (c) if necessary, converting the ring $R^{11}$ of the resultant compound of the formula

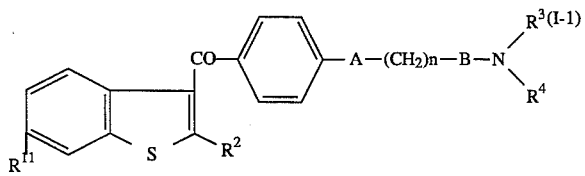   (I-1)

wherein $R^{11}$, $R^2$, $R^3$, $R^4$, A, B and n have the same meanings as above, to a hydroxyl group, an acyloxy group or an N,N-di-lower alkyl substituted or unsubstituted carbamoyloxy group, and further if necessary, converting the resultant compound to a salt.

According to the above process (a), first, the compound of the above formula (II) and the compound of the formula (III) are reacted.

The reaction can be carried out according to the Friedel-Craft's acylation reaction, and specifically, can be carried out in an inert organic solvent, for example, a halogenated hydrocarbon such as dichloromethane, 1,2-dichloroethane or chloroform; an aromatic hydrocarbon such as benzene or chlorobenzene; an alkane such as petroleum ether or hexane; a nitrohydrocarbon such as nitrobenzene or nitromethane; or the like, in the presence of a catalyst, for example, a Lewis acid such as aluminum chloride, aluminum bromide, zinc chloride, boron trifluoride, titanium tetrachloride or stannic chloride. Proper reaction temperature therefor is generally about room temperature to the reflux temperature of the reaction mixture, preferably a temperature between room temperature and 100° C.

As to the use quantity of the compound of the above formula (III) to the compound of the above formula (II), it is advantageous to use generally at least one mole, preferably 1.1 to 5 moles of the compound of the formula (III) per mole of the compound of the formula (II).

Further, as to the use quantity of the catalyst, it is preferable to use at least one, usually 1.5 to 10 moles of the catalyst per mole of the compound of the above formula (II).

Thus, the compound of the above formula (IV) is obtained, and this compound is then reacted with the amine of the above formula (V).

The reaction of the compound of the above formula (IV) with the amine of the above formula (V) can generally be carried out in the absence of solvent, or in an inert solvent, for example, an ether such as ethyl ether, tetrahydrofuran or dioxane; an amide such as dimethylformamide or dimethylacetamide; an aromatic hydrocarbon such as benzene or toluene; dimethyl sulfoxide; or the like. Proper reaction temperature therefor is usually room temperature to the reflux temperature of the reaction mixture, preferably 35° C. to the reflux temperature of the reaction mixture.

As to the use quantity of the amine of the above formula (V) to the compound of the above formula (IV), it is suitable to use generally at least one mole, usually on the order of 1.5 to 10 moles of the amine of the formula (V) per mole of the compound of the formula (IV). When the reaction is carried out in the absence of solvent, it is possible to use the amine of the formula (V) in an excess quantity and thereby make the amine play a role as a solvent.

Further, it is preferable to carry out the above reaction in the presence of a deacidifying agent, for example, an organic base such as pyridine or triethylamine, or an inorganic base such as potassium carbonate or sodium carbonate, but it is usual to use the amine in an excess quantity and thereby make the amine play a role as a deacidifying agent.

According to the above process (b), the compound of the above formula (II) and the compound of the above formula (VI) are reacted.

The reaction can be carried out in the same manner as described in the reaction of the compound of the above formula (II) with the compound of the above formula (III) in the above process (a).

Thus, the compound in the case where $R^1$ in the compounds of the above formula (I) aimed at by this invention denotes a hydrogen atom or a lower alkoxy group, namely the compound of the above formula (I-1) is obtained, and this compound can, if necessary, be converted to a compound of the above formula (I) in the case where $R^1$ denotes a hydroxyl group, an acyloxy group or an N,N-di-lower alkyl-substituted or unsubstituted carbamoyloxy group.

The conversion to the compound of the above formula (I) wherein $R^1$ denotes a hydroxyl group can be carried out by subjecting the compound of the above formula (I-1) wherein $R^{11}$ denotes a lower alkoxy group to dealkylation reaction.

The dealkylation reaction can generally be carried out by treating the compound of the above formula (I-1) in an inert solvent, for example a halogenated hydrocarbon such as dichloromethane or chloroform; an aromatic hydrocarbon such as benzene or toluene; or the like, in the coexistence of a sulfur compound such as ethanethiol or dimethyl sulfide and a Lewis acid such as aluminum chloride or boron trifluoride at an elevated temperature, preferably at the reflux temperature of the reaction mixture.

Further, the conversion to the compound of the above formula (I) wherein $R^1$ denotes an acyloxy group can easily be carried out by acylating the compound of the above formula (I) wherein $R^1$ denotes a hydroxyl group according to a process known per se, for example by reacting the compound with an acyl halide in pyridine.

Further, the conversion to the compound of the above formula (I) wherein $R^1$ denotes an N,N-di-lower alkyl-substituted or unsubstituted carbamoyloxy group can also be carried out easily by a process known per se, for example by reacting the compound of the above formula (I) wherein $R^1$ denotes a hydroxyl group with a substituted or unsubstituted carbamoyl chloride in pyridine.

In the compounds of the above formula (I) prepared according to the above-described processes, a compound wherein B denotes $CH_2$ can be converted to a corresponding salt by treating it with an inorganic acid or an organic acid according to a process known per se.

The thus obtainable compound of the above formula (I) can be separated from the reaction mixture and purified by methods such as, for example, extraction, filtration, distillation, recrystallization, column chromatography and thin layer chromatography.

A compound in the case where B denotes $CH_2$ in the compounds of the above formula (I-1) of this invention can, alternatively, be prepared by reducing a compound of the following formula

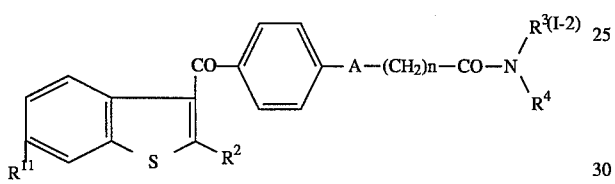

(I-2)

wherein $R^{11}$, $R^2$, $R^3$, $R^4$, A and n have the same meanings as above, and then oxidizing the resultant compound.

The reduction of the compound of the formula (I-2) can, for example, be carried out by treating it with lithium aluminum hydride in a solvent such as tetrahydrofuran or dioxane under reflux with heating. The oxidation of the resultant compound of the following formula

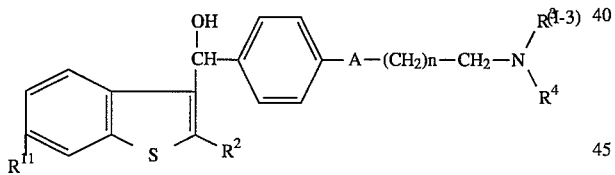

(I-3)

wherein $R^{11}$, $R^2$, $R^3$, $R^4$, A and n have the same meanings as above, can easily be carried out by treating it with chromium trioxide in pyridine.

In the compounds of the above formula (I) of this invention, a compound wherein $R^2$ denotes a cycloalkyl or cycloalkenyl group substituted by a hydroxyl group can, for example, be prepared by reducing a compound of the formula (I) wherein $R^2$ denotes a cycloalkyl or cycloalkenyl group substituted by an oxo group with a complex metal hydride such as sodium borohydride in a solvent such as tetrahydrofuran.

Further, a compound of the formula (I) wherein $R^2$ is a cycloalkyl or cycloalkenyl group substituted by an acyloxy group can be prepared by acylating a compound of the formula (I) wherein $R^2$ is a cycloalkyl or cycloalkenyl group substituted by a hydroxyl group, according to a process known per se. In this reaction, when a compound of the formula (I) wherein $R^1$ is a hydroxyl group is used, $R^1$ is acylated simultaneously and converted to an acyloxy group.

Among the compounds of the above formula (II) used as a starting compound in the foregoing processes, compounds wherein $R^{11}$ denotes a lower alkoxy group, namely compounds of the following formula

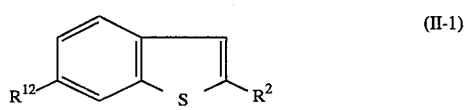

(II-1)

wherein $R^{12}$ denotes a lower alkoxy group and $R^2$ has the same meaning as above, are novel compounds not disclosed in the past literatures, and are important intermediates for synthesis of the compounds of the above formula (I) of this invention having a strong antiestrogenic activity.

The compounds of the above formula (II) as a starting material for the compounds of this invention can, for example, by synthesized according to the following Reaction formula 1.

Reaction formula 1

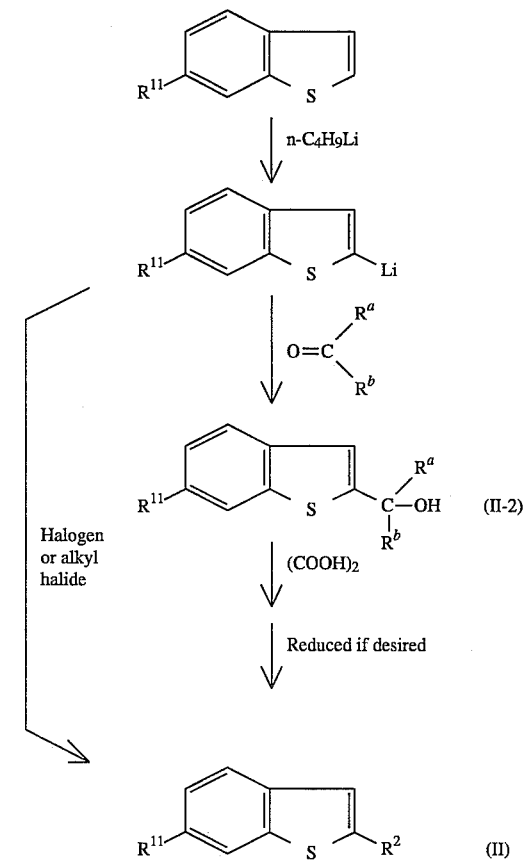

In the above formulae, $R_a$ and $R_b$ each denote a lower alkyl group, or combine with the carbon atom to which they bind to denote a cycloalkyl group optionally substituted by a lower alkyl group or an oxo group, and $R^{11}$ has the same meaning as above.

As to the detail of reaction conditions in Reaction formula 1, please see the later-described preparation examples.

Further, a compound of the formula (II) wherein $R^2$ denotes a cycoakyl or cycloalkenyl group substituted by a hydroxyl group or an acyloxy group can be synthesized by converting a compound wherein $R^2$ denotes a cycloalkyl or cycloalkenyl group substituted by an oxo group, in the same manner as described in the conversion of $R^2$ in a compound of the formula (I).

Effect of the Invention

The thus described benzothiophene derivatives represented by the formula (I) of this invention have an excellent antiestrogenic activity, and are effective for curing or treatment of estrogen-dependent diseases such as, for example, breast cancer, endometrial cancer, endometriosis, prostatic hypertrophy and mastopathy.

The antiestrogenic activities of the compounds of the formula (I) of this invention are as follows.

Assay of Antiestrogenic Activity

Assay was carried out according to the juvenile rat uterus weight method using groups of immature female rats (weight 50 to 60 g), each group consisting of 5 animals.

Namely, 2 μg/animal of estradiol and a test compound were subcutaneously administered to rats once a day for 3 days, the rats were killed on the fourth day, and each uterus was weighed. Antiestrogenic activity was assessed depending on whether or not the weight of the uterus of the group to which estradiol and the test compound were administered is significantly inhibited in comparison with the weight of the uterus of the group to which estradiol alone was administered.

The results are shown in the following table. As to antiestrogenic activity, when 0.1 mg/kg each of test compounds were administered, those inhibiting the uterine weight significantly at a level of significance of 1% and those inhibiting the uterine weight significantly at a level of significance of 5% were expressed by ++ and +, respectively.

TABLE

| Compound | Antiestrogenic activity |
| --- | --- |
| Example 71 | ++ |
| Example 74 | ++ |
| Example 75 | ++ |
| Example 76 | ++ |
| Example 77 | ++ |
| Example 86 | ++ |
| Example 87 | ++ |
| Example 90 | ++ |
| Example 91 | ++ |
| Example 93 | + |
| Example 96 | + |
| Example 104 | + |
| Example 115 | + |
| Example 118 | ++ |
| Example 120 | ++ |
| Example 123 | + |
| Example 124 | ++ |
| Example 130 | + |

Thus, the compounds of this invention represented by the formula (I) can be orally or parenterally (for example, intramuscularly, intravenously, rectally, transcutaneously, or the like) administered as an antiestrogenic agent for curing or treatment of human beings and other mammals.

The compounds of this invention, when used as a drug, can be used by formulating them into any dosage form of solid forms (e.g., tablets, hard capsules, soft capsules, granules, powders, fine granules, pills, troches, etc.), semi-solid forms (e.g., suppositories, ointments, etc.) and liquid forms (e.g., injections, emulsions, suspensions, lotions, sprays, etc.). An nontoxic additives usable in the above formulations, there can, for example, be mentioned starches, gelatin, glucose, lactose, fructose, maltose, magnesium carbonate, talc, magnesium stearate, methylcellulose, carboxymethylcellulose or salts thereof, gum arabic, polyethylene glycol, p-hydroxybenzoic acid alkyl esters, syrups, ethanol, propylene glycol, vaselines, carbowax, glycerol, sodium chloride, sodium sulfite, sodium phosphate, citric acid, etc. The drug can also contain another therapeutically effective drug.

The content of the compound of this invention in the drug varies depending on the dosage form, but it is generally preferable that the drug contains the compound at a concentration of 0.1 to 50 wt. % in the case of solid and semi-solid forms, and at a concentration of 0.05 to 10 wt. % in the case of liquid form.

The dose of the compound of this invention can widely be varied depending on the kind of warm-blooded animals including human beings as a subject, administration routes, the seriousness of symptoms, the diagnoses of doctors, etc., but can be generally 0.05 to 50 mg/kg, preferably 0.1 to 10 mg/kg per day. However, it is of course be possible to administer the compound in an amount smaller than the lower limit of the above range or in an amount larger than the upper limit thereof in accordance with the seriousness of the symptom of the patient and the diagnosis of the doctor as mentioned above. The above dose can be administered once a day or in divided several portions per day.

This invention is further described below according to examples and preparation examples.

Preparation Example 1

3.2 g of 6-methoxybenzo[b]thiophene was dissolved in 3 ml of THF and the solution was cooled with ice. 18.6 ml of n-butyllithium (15% hexane solution) was gradually added in a stream of nitrogen and the mixture was stirred. A THF solution of 3.1 ml of cyclohexanone was added and the mixture was stirred at room temperature for 6 hours. 35 ml of saturated aqueous ammonium chloride solution was added to the reaction mixture, the resultant mixture was extracted with ether, and the extract was dried over anhydrous magnesium sulfate. The solvent was distilled off, and the resultant crude product was purified by TLC (developing solvent, chloroform) to obtain 2.8 g of 6-methoxy-2-(1-hydroxycyclohexyl)benzo[b]thiophene.

$^1$H-NMR(CDCl$_3$, δ):1.33~2.03(10H, m), 3.85(3H, s), 6.94(1H, dd, J=2.4, 8.6 Hz), 7.09(1H, s), 7.27(1H, d, J=2.4 Hz), 7.57(1H, d, J=8.6 Hz).

MS(m/z):262(M$^+$), 244, 219.

The following compounds of (i) to (ix) were synthesized in the same manner as in Preparation example 1.

(i) 6-Methoxy-2-(1-hydroxycyclopentyl)benzo[b]thiophene $^1$H-NMR(CDCl$_3$, δ):1.58~2.86(8H, m), 3.85(3H, s), 6.86(1H, d, J=2.4 Hz), 6.94(1H, s), 7.22(1H, d, J=2.4 Hz), 7.54(1H, d, J=8.6 Hz).

MS(m/z):248(M$^+$), 230.

(ii) 6-Methoxy-2-[4,4-(ethylenedioxy)-1-hydroxycyclohexyl]benzo[b]thiophene $^1$H-NMR(CDCl$_3$, δ):1.30~2.50(8H, m), 3.85(3H, s), 3.97(4H, s), 6.94 (1H, dd, 1:8.8, 2.4 Hz), 7. 10(1H, br, s), 7.27(1H, d, J:2.4 Hz), 7.55(1H, d, J= 8.8 Hz).

MS(m/z):320(M$^+$), 302, 216, 101.

(iii) 6-Methoxy-2-(1-hydroxycycloheptyl)benzo[b]thiophene $^1$H-NMR(CDCl$_2$δ):1.46~2. 71 (13H, m), 3.84(3H, s), 6.90(1H; dd, J=8.8, 2.4 Hz), 7.07(1H, d. J=0.4 Hz), 7.20(1H, d, J=2.2Hz), 7.51(1H, d, J=8.6 Hz).

Ms(m/z):276(M$^+$), 258.

(iv) 6-Methoxy-2-[1-hydroxy-(2-methylcyclohexyl)]

benzo[b]thiophene

¹H-NMR(CDCl₃, δ):0.82(3H, d, J=6.6 Hz), 1.54~1.94(10H, m), 3.85(3H, s), 6.94(1H, dd, J=8.6, 2.4 Hz), 7.03(1H, d, J=0.4 Hz), 7.26(1H, d, J=2.9 Hz), 7.50(1H, d, J=8.6 Hz).

MS(m/z):276(M⁺), 219.

(v) 6-Methoxy-2-[1-hydroxy-(3-methylcyclohexyl)]benzo[b]thiophene

¹H-NMR(CDCl₃, δ):0.94(3H, d, J=6.2 Hz), 1.45~2.11(10H, m), 3.85(3H, s), 6.94(1H, dd, J=8.6, 2.4 Hz), 7.06(1H, d, J=0.4 Hz), 7.27(1H, d, J=2.9 Hz), 7.56(1H, d, J=8.8 Hz).

MS(m/z):276(M⁺), 233.

(vi) 6-Methoxy-2-[1-hydroxy-(4-methylcyclohexyl)]benzo[b]thiophene

¹H-NMR(CDCl₃, δ):1.01(3H, d, J=5.9 Hz), 1.23~2.56(10H, m), 3.89(3H, s), 6.93(1H, dd, J=6.4, 1.8 Hz), 7.07(1H, d, J=0.7 Hz), 7.20~7.28(1H, m), 7.66(1H, d, J=8.6 Hz).

MS(m/z):276(M⁺), 219.

(vii) 6-Methoxy-2-(1-hydroxycyclooctyl)]benzo[b]thiophene

¹H-NMR(CDCl₃δ):1.40~1.88(10H, m), 2.10~2.79(4H, m), 3.85(3H, s), 6.18(1H, t, J=8.1 Hz), 6.89(1H, dd, J=8.8, 3.4 Hz), 7.05(1H, s), 7.21 (1H, d, J=2.4 Hz), 7.52(1H, d, J=8.6 Hz).

MS(m/z):290(M⁺), 272, 244.

(viii) 6-Methoxy-2-(1-hydroxycyclododecyl)benzo[b]thiophene

¹H-NMR(CDCl₃, δ):1.23~2.66(23H, m), 3.85(3H, s), 6.93(1H, dd, J=8.6, 2.4 Hz), 7.03(1H, s), 7.25(1H, d, J=4.6 Hz), 7.51(1H, d, J=8.8 Hz).

MS(m/z):346(M⁺), 328, 204.

(ix) 6-Methoxy-2-(1-hydroxy-1-methylethyl)benzo[b]thiophene

Preparation Example 2

2.8 g of 6-methoxy-2-(1-hydroxycyclohexyl)benzo[b]thiophene was dissolved in 25 ml of toluene, 320 mg of anhydrous oxalic acid was added, and the mixture was refluxed with heating for 1 hour. The reaction mixture was washed twice with 5% aqueous sodium bicarbonate solution and once with water, and dried over magnesium sulfate. The solvent was distilled off to obtain 20 2.5 g of 6-methoxy-2-(1-cyclohexenyl)benzo[b]thiophene.

¹H-NMR(CDCl₃, δ):1.49~2.51(8H, m), 3.84(3H, s), 6.20(1H, br), 6.89 (1H, rid, J=2.4, 8.8 Hz), 7.00(1H, br), 7.21 (1H, d, J=2.4 Hz), 7.52(1H, d, J= 8.8 Hz).

MS(m/z):244(M⁺).

The following compounds of (i) to (ix) were synthesized in the same manner as in Preparation example 2.

(i) 6-Methoxy-2-(1-cyclopentenyl)benzo[b]thiophene

¹H-NMR(CDCl₃, δ):1.49~2.89(6H, m), 3.85(3H, s), 6.05(1H, m), 6.86 (1H, dd, J=8.6, 2.4 Hz), 6.97(1H, s), 7.22(1H, d, J=2.4 Hz), 7.54(1H, d, J= 8.6 Hz).

MS(m/z):230(M⁺), 215.

(ii) 6-Methoxy-2-(4-oxo-1-cyclohexenyl)benzo[b]thiophene (iii) 6-Methoxy-2-( 1-cycloheptenyl)benzo[b]thiophene ¹H-NMR(CDCl₃, δ):1.47~1.90(6H, m), 2.30(2H, q, J=6.8, 3.5 Hz), 2.60~ 2.71 (2H, m), 3.85(3H, s), 6.35(1H, t, J=6.8 Hz), 6.89(1H, dd, J=8.6, 2.4 Hz), 7.02(1H, s), 7.20(1H, d, J=2.2 Hz), 7.51(1H, d, J=8.6 Hz).

MS(m/z):258(M⁺), 231.

(iv) 6-Methoxy-2-[1-(2-methylcyclohexenyl)]benzo[b]thiophene

¹H-NMR(CDCl₃, δ):1.21(3H, d, J=7.0 Hz), 1.52~1.85(4H, m), 2.10~ 2.29(2H, m), 2.75~2.89(1H, br s), 3.85(3H, s), 6.11(1H, t, J=3.7 Hz), 6.90(1H, dd, J=8.6, 2.4 Hz), 7.02(1H, s), 7.22(1H, d, J=2.4 Hz), 7.53(1H, d, J=8.6 Hz).

MS(m/z):258(M⁺).

(v) 5-Methoxy-2-[1-(3-methylcyclohexenyl)]benzo[b]thiophene

¹H-NMR(CDCl₃, δ):1.07(3H, d, J=5.9 Hz), 1.24~2.50(7H, m), 3.84(3H, s), 6.11(1H, d, J=12.5 Hz), 6.90(1H, dd, J=8.6, 2.4 Hz), 7.01(1H, s), 7.21 (1H, d, J=2.4 Hz), 7.52(1H, d, J=8.6 Hz).

MS(m/z):258(M⁺).

(vi) 6-Methoxy-2-[1-(4-methylcyclohexenyl)]benzo[b]thiophene

¹H-NMR(CDCl₃, δ):1.01(3H, d, J=5.7 Hz), 1.26~2.59(7H, m), 3.84(3H, s), 6.12~6.19(1H, br s), 6.89(1H, dd, J=8.6, 2.4 Hz), 7.00(1H, s), 7.21 (1H, d, J=2.4 Hz), 7.52(1H, d, J=8.6 Hz).

MS(m/z):258(M⁺), 216.

(vii) 6-Methoxy-2-(1-cyclooctenyl)benzo[b]thiophene

¹H-NMR(CDCl₃, δ):1.54~1.83(8H, m), 2.21~2.40(2H, m), 2.69(2H, t, J= 5.1 Hz), 3.84(3H, s), 6.18(1H, t, J=8.1 Hz), 6.89(1H, dd, J=8.6, 2.4 Hz), 7.04(1H, s), 7.21(1H, d, J=2.4 Hz), 7.52(1H, d, J=8.6 Hz).

MS(m/z):272(M⁺), 244.

(viii) 6-Methoxy-2-(1-cyclododecenyl)benzo[b]thiophene

¹H-NMR(CDCl₃, δ):1.23~1.80(16H, m), 2.26(2H, q, J=7.5, 7.0 Hz), 2.59 (2H, t, J=6.8 Hz), 3.84(3H, s), 5.93(1H, t, J=8.1 Hz), 6.90(1H, dd, J=8.6, 2.4 Hz), 7.04(1H, s), 7.21 (1H, d, J=2.4 Hz), 7.52(1H, d, J=8.6 Hz).

MS(m/z):328(M⁺), 204.

(ix) 6-Methoxy-2-isopropenylbenzo[b]thiophene

Preparation Example 3

5 g of 6-methoxy-2-(1-cyclohexenyl)benzo[b]thiophene was dissolved in 20 ml of ethyl acetate, 800 mg of 5% palladium-carbon was added, and hydrogenation was carried out at room temperature and at atmospheric pressure. The reaction mixture was filtered, and the filtrate was concentrated to obtain 2.5 g of 6-methoxy-2-cyclohexylbenzo[b]thiophene.

¹H-NMR(CDCl₃, δ):1.15~2.21(10H, m), 2.82(1H, m), 3.84(3H, s), 6.83~ 7.57(4H, m).

MS(m/z):246(M⁺).

The following compounds of (i) to (viii) were synthesized in the same manner as in Preparation example 3.

(i) 6-Methoxy-2-cyclopentylbenzo[b]thiophene

¹H-NMR(CDCl₃, δ):1.46~2.30(8H, m), 3.27(1H, m), 3.84(3H, s), 6.91 (1H, s), 6.94(1H, dd, J=8.6, 2.4 Hz), 7.25(1H, d, J=2.4 Hz), 7.52(1H, d, J= 8.6 Hz).

MS(m/z):232(M⁺), 203.

(ii) 6-Methoxy-2-(4-oxo-1-cyclohexyl)benzo[b]thiophene

¹H-NMR(CDCl₃, δ):1.50~2.70(8H, m), 3.35(1H, m), 3.85(3H, s), 6.96 (1H, dd, J=8.6, 2.4 Hz), 6.98(1H, br s), 7.28(1H, d, J=2.4 Hz), 7.55(1H, d, J= 8.6 Hz).

(iii) 6-Methoxy-2-cycloheptylbenzo[b]thiophene

¹H-NMR(CDCl₃, δ):1.41~2.25(12H, m), 2.89~3.09(1H, m), 3.83(3H, s), 6.91(1H, dd, J=8.6, 2.4 Hz), 6.87(1H, s), 7.24(1H, d, J=2.0 Hz), 7.51(1H, d, J=8.6 Hz).

MS(m/z):260(M⁺), 203.

(iv) 6-Methoxy-2-(2-methylcyclohexyl)benzo[b]thiophene

¹H-NMR(CDCl₃, δ):0.80(3H, d, J=7.0 Hz), 1.20~2.40(9H, m), 2.98~ 3.13(1H, m), 3.83(3H, s), 6.85(1H, s), 6.91 (1H, dd, J=8.8, 2.4 Hz), 7.25(1H, d, J=2.4 Hz), 7.53(1H d, J=8.6 Hz).

MS(m/z):260(M⁺), 203.

(v) 5-Methoxy-2-(3-methylcyclohexyl)benzo[b]thiophene

¹H-NMR(CDCl₃, δ):0.95(3H, d, J=5.9 Hz), 1.19~2.20(9H, m), 3.10~ 3.28(1H, m), 3.84(3H, s), 6.88(1H, s), 6.91(1H, dd, J=8.6, 2.4 Hz), 7.25(1H, d, J=1.5 Hz), 7.52(1H, d, J=8.8 Hz).

MS(m/z):260(M⁺).

(vi) 6-Methoxy-2-(4-methylcyclohexyl)benzo[b]thiophene

¹H-NMR(CDCl₃, δ):0.94(3H, d, J=6.4 Hz), 1.20~2.20(9H, m), 2.95~ 3.08(1H, m), 3.83(3H, s), 6.91 (1H, dd, J=8.6, 2.4 Hz), 6.94(1H, s), 7.24(1H, d, J=2.4 Hz), 7.52 (1H, d, J=8.8 Hz).

MS(m/z):260(M⁺), 203.

(vii) 6-Methoxy-2-cyclododecylbenzo[b]thiophene

¹H-NMR(CDCl₃, δ):1.14~1.97(22H, m), 3.01~3.15(1H, m), 3.84(3H, s), 6.91 (1H, dd, J=8.8, 2.4 Hz), 6.90(1H, s), 7.25(1H, d, J=2.2 Hz), 7.52(1H, d, J=8.6 Hz).

MS(m/z):330(M⁺).

(viii) 6-Methoxy-2-isopropylbenzo[b]thiophene

¹H-NMR(CDCl₃, δ):1.37(6H, d, J=7.8 Hz), 3.04~3.35(1H, m), 3.84(3H, s), 6.92(1H, dd, J=8.6, 2.4 Hz), 6.89(1H, s), 7.25(1H, d, J=2.4 Hz), 7.52(1H, d, J=8.6 Hz).

MS(m/z):206(M⁺), 191.

Preparation Example 4

The same operations as in Preparation example 1 were carried out using 180 mg of 6-methoxybenzo[b]thiophene, and 450 mg of methyl iodide in place of cyclohexanone, and then purification was carried out by TLC (developing solvent, chloroform:n-hexane=1:19) to obtain 126 mg of 6-methoxy-2-methylbenzo[b]thiophene.

¹H-NMR(CDCl₃, δ):2.53(3H, s), 3.85(3H, s), 6.85~7.56(4H, m).

MS(m/z):164(M⁺).

Preparation Example 5

The same operations as in Preparation example 1 were carried out using 495 mg of 6-methoxybenzo[b]thiophene, and chlorine gas in place of cyclohexanone, and then purification was carried out by TLC (developing solvent, chloroform:n-hexane=4:1) to obtain 172 mg of 6-methoxy-2-chlorobenzo[b]thiophene.

¹H-NMR(CDCl₃, δ):3.85(3H, s), 6.89~7.73(4H, m).

MS(m/z):200, 198.

Preparation Example 5

50 mg of 4-(2-chloroethoxy)benzoic acid was refluxed with heating together with 0.5 ml of thionyl chloride and 1 ml of 1,2-dichloroethane for 2 hours to convert it to an acid chloride. The resultant acid chloride was concentrated under reduced pressure to distill off 1,2-dichloroethane and thionyl chloride, and the residue was mixed with 50 mg of 5-methoxy-2-cyclohexylbenzo[b]thiophene, 7 ml of dichloromethane and 200 mg of aluminum chloride, followed by stirring at room temperature for 3 hours. 1 ml of THF, 0.3 ml of 20% hydrochloric acid and 1 ml of water were added to the reaction mixture at 25° C. or lower, and the mixture was made alkaline with saturated aqueous sodium bicarbonate solution and then extracted with ethyl acetate. The organic layer was dried over anhydrous magnesium sulfate, the solvent was distilled off, and the resultant crude product was purified by TLC (developing solvent, chloroform:n-hexane= 2:1) to obtain 41 mg of (6-methoxy-2-cyclohexylbenzo[b]thien-3-yl)[4-(2-chloroethoxy)phenyl] methanone.

¹H-NMR(CDCl₃, δ):1.09~3.11(11H, m), 3.76~3.88(5H, m), 3.83(3H, s), 4.28(2H, t, J=5.5 Hz), 6.77~8.04(7H, m).

MS(m/z):430, 428.

The following compounds of (i) to (ix) were synthesized in the same manner as in Preparation example 6.

(i) (6-Methoxy-2-cyclohexylbenzo[b]thien-3-yl)[4-(2-chloropropoxy)phenyl]methanone ¹H-NMR(CDCl₃, δ):1.12~2.41(12H, m), 3.00(1H, m), 3.74(2H, t, J=6 Hz) 3.84(3H, s), 4.19(2H, t, J=6 Hz), 6.76~8.04(7H, m).

MS(m/z):444, 442.

(ii) [6-Methoxy-2-(2-methylcyclohexyl)benzo[b]thien-3yl][4-(2-chloroethoxy)phenyl]methanone ¹H-NMR(CDCl₃, δ):0.72~2.46(12H, m), 3.82(2H, t, J=5.8 Hz), 3.88(3H, s), 4.31 (2H, t, J=5.8 Hz), 6.76~8.04(7H, m).

MS(m/z):444, 442.

(iii) (6-Methoxy-2-cycloheptylbenzo[b]thien-3-yl)[4-(2-chloroethoxy)phenyl]methanone ¹H-NMR(CDCl₃, δ):1.26~2.17(12H, m), 3.16(1H, m), 3.81(2H, t, J=5.7 Hz), 3.84(3H, s), 4.28(2H, br t), 6.78~8.08(7H, m).

MS(m/z):444, 442.

(iv) (6-Methoxy-2-cycloheptylbenzo[b]thien-3-yl)[4-(2-chloropropoxy)phenyl]methanone ¹H-NMR(CDCl₃, δ):1.26~2.33(14H, m), 3.75(2H, t, J=6 Hz), 3.85(3H, s), 4.19(2H, t, J=6 Hz), 6.78~8.04(7H, m).

MS(m/z):458, 456.

(v) [6-Methoxy-2-(3-methylcyclohexyl)benzo[b]thien-3-yl][4-(2-chloroethoxy)phenyl]methanone ¹H-NMR(CDCl₃, δ):0.78~2.08(12H, m), 3.81(2H, t, J=5.7 Hz), 3.83(3H, s), 4.30(2H, br t), 6.78~8.08(7H, m).

MS(m/z):444, 442.

(vi) (6-Methoxy-2-cyclopentylbenzo[b]thien-3-yl)[4-(2-chloroethoxy)phenyl]methanone ¹H-NMR(CDCl₃, δ):1.25~2.21(8H, m), 3.33(1H, m), 3.75~3.88(5H, m), 4.28(2H, t, J=5.6 Hz), 6.79~8.04(7H, m).

MS(m/z):416, 414.

(vii) (6-Methoxy-2-cyclopentylbenzo[b]thien-3-yl)[4-(2chloropropoxy)phenyl]methanone ¹H-NMR(CDCl₃, δ):1.22~2.42(10H, m), 3.36(1H, m), 3.74(2H, t, J=5.9 Hz), 3.84(3H, s), 4.18(2H, t, J=5.9 Hz), 6.79~8.01 (7H, m).

MS(m/z):430, 428.

(viii) (6-Methoxy-2-cyclododecylbenzo[b]thien-3-yl)[4-(2-chloroethoxy)phenyl]methanone ¹H-NMR(CDCl₃, δ):1.15~2.10(22H, m), 2.90~3.20(1H, m), 3.76(3H, s), 3.82(2H, t, J=5.3 Hz), 4.29(2H, t, J=5.5 Hz), 6.85(1H, dd, J=7.0, 2.2 Hz), 6.90(2H, d, J=9.0 Hz), 7.25~7.58(2H, m), 7.76(2H, d, J=9.0 Hz).

MS(m/z):512(M⁺), 329, 183.

(ix) (6-Methoxy-2-isopropylbenzo[b]thien-3-yl)[4-(2-chloroethoxy)phenyl]methanone ¹H-NMR(CDCl₃, δ):1.31(6H, d, J=6.8 Hz), 3.19~3.49(1H, m), 3.83(2H, t, J=5.9 Hz), 3.85(3H, s), 4.30(2H, t, J=5.5 Hz), 6.93(1H, d, J=8.8 Hz), 6.85 (1H, dd, J=8.8, 2.4 Hz), 6.85~6.96(1H, m), 7.24(2H, d, J=8.6 Hz), 7.84(2H, d, J=9.0 Hz).

MS(m/z):388($M^+$), 373.

Preparation Example 7

353 mg of (6-methoxy-2-cyclohexylbenzo[b]thien-3-yl)[4-[2-(1-piperidinylcarbonyl)ethyl]phenyl]methanone was dissolved in 30 ml of THF, 850 mg of lithium aluminum hydride was added, and the mixture was refluxed with heating for 1 hour. A small quantity of water was added to the reaction mixture, followed by stirring, 1 ml of methanol was added, followed by stirring for 5 minutes, and 5 ml of ethyl acetate was added, followed by stirring for 5 minutes. The mixture was filtered using a super cell, the filtrate was concentrated under reduced pressure, and the resultant crude product was purified by TLC (developing solvent, chloroform:methanol=19:1) to obtain 107 mg of (6-methoxy-2-cyclohexylbenzo[b]thien-3-yl)[4-[3-(1-piperidinyl)propyl]phenyl]methanol.

$^1$H-NMR(CDCl$_3$, δ):1.26~2.86(26H, m), 3.4(1H, m), 3.85(3H, s), 6.26 (1H, s), 6.71~7.60(7H, m).

MS(m/z):477($M^+$), 98.

The following compounds of (i) to (iv) were synthesized in the same manner as in Preparation example 7.

(i) (6-Methoxy-2-cycloheptylbenzo[b]thien-3-yl)[4-[3-(1-piperidinyl)propyl]phenyl]methanol $^1$H-NMR(CDCl$_3$, δ):1.25~2.80(28H, m), 3.34(1H, m), 3.80(3H, s), 6.26 (1H, s), 6.72~7.53(7H, m).

MS(m/z):491($M^+$), 98.

(ii) (6-Methoxy-2-cyclohexylbenzo[b]thien-3-yl)[4-[3-(dimethylamino)propyl]phenyl]methanol $^1$H-NMR(CD$_3$OD, δ):1.21~2.05(10H, m), 2.29(6H, s), 2.29~2.68(2H, m), 3.47~3.72(4H, m), 3.78(3H, s), 6.21(1H, s), 6.68~7.58(7H, m).

MS(m/z):437($M^+$), 58.

(iii) (6-Methoxy-2-cyclohexylbenzo[b]thien-3-yl)[4-[3-(1-pyrrolidinyl)propyl]phenyl] methanol $^1$H-NMR(CDCl$_3$, δ):1.10~2.05(16H, m), 2.45~2.78(8H, m), 2.85~3.50 (1H, m), 3.80(3H, s), 6.26(1H, s), 6.71~7.52(7H, m).

MS(m/z):463($M^+$), 84.

(iv) (6-Methoxy-2-cyclohexylbenzo[b]thien-3-yl)[4-[4-(1-pyrrolidinyl)butyl]phenyl]methanol

EXAMPLE 1

1 ml of pyrrolidine was added to 30 mg of (6-methoxy-2-cyclopentylbenzo[b]thien-3-yl)[4-(2-chloroethoxy)phenyl]methanone, followed by reflux with heating for 1 hour. The mixture was concentrated under reduced pressure to distil off pyrrolidine, and the residue was purified by TLC (developing solvent, chloroform:methanol= 19:1) to obtain 28 mg of (6-methoxy-2-cyclopentylbenzo[b]thien-3-yl)[4-[2-(1-pyrrolidinyl)ethoxy]phenyl]methanone.

$^1$H-NMR(CDCl$_3$, δ):0.94~2.47(12H, m), 2.55~2.79(4H, m), 2.94(2H, t, J=6 Hz), 3.41(1H, m), 3.84(3H, s), 4.19(2H, t, J=6 Hz), 6.79~7.87(7H, m).

MS(m/z):449($M^+$), 84.

The following compounds of Examples 2–31 were synthesized in the same manner as in Example 1.

EXAMPLE 2

(6-Methoxy-2-cyclopentylbenzo[b]thien-3-yl)[4-[2-(1-homopiperidinyl)ethoxy]phenyl]methanone $^1$H-NMR(CDCl$_3$, δ):1.25~2.16(16H, m), 2.77~2.92(4H, m), 2.94(2H, t, J=6 Hz), 3.3(1H, m), 3.84(3H, s), 4.12(2H, t, J=6 Hz), 6.79~7.87(7H, m).

MS(m/z):477($M^+$), 112.

EXAMPLE 3

(6-Methoxy-2-cyclopentylbenzo[b]thien-3-yl)[4-[2-[1-(3-methylpiperidinyl)]ethoxy] phenyl]methanone $^1$H-NMR(CDCl$_3$, δ):0.89(3H, d, J=5.9 Hz), 1.25~2.23(15H, m), 2.87~3.60(5H, m), 3.84(3H, s), 4.26(2H, t, J=5.7 Hz), 6.79~7.87(7H, m).

MS(m/z):477($M^+$), 112.

EXAMPLE 4

(6-Methoxy-2-cyclohexylbenzo[b]thien-3-yl)[4-[2-[1-(4-methylpiperazinyl)]ethoxy] phenyl]methanone $^1$H-NMR(CDCl$_3$, δ):1.12~2.07(10H, m), 2.32(3H, s), 2.37~2.75(8H, m), 2.84(2H, t, J=5.7 Hz), 3.84(3H, s), 4.17(2H, t, J=5.7 Hz), 6.77~7.88(7H, m).

MS(m/z):492($M^+$), 113.

EXAMPLE 5

(6-Methoxy-2-cyclohexylbenzo[b]thien-3-yl)[4-[2-[2-(1,2,3,4-tetrahydroisoquinolinyl)] ethoxy]phenyl]methanone $^1$H-NMR(CDCl$_3$, δ):1.10~2.16(10H, m), 2.61~3.09(7H, m), 3.84(5H, m), 4.28(2H, t, J=5.7 Hz), 6.76~7.87(11H, m).

MS(m/z):525($M^+$), 146.

EXAMPLE 6

(6-Methoxy-2-cyclohexylbenzo[b]thien-3-yl)[4-[2-[1-(4-hydroxypiperidinyl)]ethoxy] phenyl]methanone $^1$H-NMR(CDCl$_3$, δ):112~2.16(14H, m), 2.34~3.07(7H, m), 3.69~3.84 (4H, m), 4.23(2H, t, J=5.7 Hz), 6.78~7.86(7H, m).

MS(m/z):493($M^+$), 114.

EXAMPLE 7

(6-Methoxy-2-cyclohexylbenzo[b]thien-3-yl)[4-[2-(diethylamino)ethoxy]phenyl]methanone $^1$H-NMR(CDCl$_3$, δ):0.77~2.13(16H, m), 2.72(4H, q), 2.96(2H, t, J=6 Hz), 3.84(3H, s), 4.18(2H, t, J=6 Hz), 6.78~7.85(7H, m).

MS(m/z):465($M^+$), 86.

EXAMPLE 8

(6-Methoxy-2-cycloheptylbenzo[b]thien-3-yl)[4-[2-(1-pyrrolidinyl)ethoxy]phenyl]methanone $^1$H-NMR(CDCl$_3$, δ):1.22~2.24(16H, m), 2.55~2.72(4H, m), 2.94(2H, t, J=5.9 Hz), 3.2(1H, m), 3.84(3H, s), 4.19(2H, t, J=5.9 Hz), 6.78~8.03(7H, m).

MS(m/z):477 ($M^+$), 84.

EXAMPLE 9

(6-Methoxy-2-cycloheptylbenzo[b]thien-3-yl)[4-[2-(1-homopiperidinyl)ethoxy]phenyl]methanone $^1$H-NMR(CDCl$_3$, δ):1.25~2.16(20H, m), 2.79~2.85(4H, m), 3.03(2H, t, J=5.9 Hz), 3.84(3H, s), 4.18(2H, t, J=5.9 Hz), 6.78~7.85(7H, m).

MS(m/z):505($M^+$), 112.

EXAMPLE 10

(6-Methoxy-2-cycloheptylbenzo[b]thien-3-yl)[4-[2-[1-(3-methylpiperidinyl)]ethoxy] phenyl]methanone $^1$H-NMR(CDCl$_3$, δ):0.92(3H, d, J=5.9 Hz), 1.12~2.69(19H, m), 2.60~ 3.25(5H, m), 3.83(3H, s), 4.19(2H, t, J=5.9 Hz), 6.78~8.00(7H, m).

MS(m/z):505(M$^+$), 112.

EXAMPLE 11

[6-Methoxy-2-(2-methylcyclohexyl)benzo[b]thien-3-yl][4-[2-(1-pyrrolidinyl)ethoxy] phenyl]methanone $^1$H-NMR(CDCl$_3$, δ):0.84(3H, d, J=7.0 Hz), 1.13~2.15(13H, m), 2.57~ 2.89(4H, m), 2.97(2H, t, J=5.8 Hz), 3.4(1H, m), 3.84(3H, s), 4.21(2H, t, J=5.8 Hz), 6.77~7.85(7H, m).

MS(m/z):477(M$^+$), 84.

EXAMPLE 12

[6-Methoxy-2-(2-methylcyclohexyl)benzo[b]thien-3-yl][4-[2-(1-piperidinyl)ethoxy] phenyl]methanone $^1$H-NMR(CDCl$_3$, δ):0.80(3H, d, J=7.0 Hz), 1.13~2.29(15H, m), 2.53(4H, m), 2.79(2H, t, J=6 Hz), 3.3(1H, m), 3.84(3H, s), 4.17(2H, t, J=6 Hz), 6.77~7.85(7H, m).

MS(m/z):491(M$^+$), 98.

EXAMPLE 13

[6-Methoxy-2-(2-methylcyclohexyl)benzo[b]thien-3-yl][4-[2-(1-homopiperidinyl)ethoxy] phenyl]methanone $^1$H-NMR(CDCl$_3$, δ):0.83(3H, d, J=7.0 Hz), 1.13~2.07(17H, m), 2.75~ 2.88(4H, m), 3.01(2H, t, J=6.2 Hz), 3.4(1H, m), 3.84(3H, s), 4.17(2H, t, J=6.2 Hz), 6.62~7.85(7H, m).

MS(m/z):505(M$^+$), 112.

EXAMPLE 14

[6-Methoxy-2-(3-methylcyclohexyl)benzo[b]thien-3-yl][4-[2-(1-pyrrolidinyl)ethoxy] phenyl]methanone $^1$H-NMR(CDCl$_3$, δ):0.88(3H, d, J=5.3 Hz), 1.03~2.68(13H, m), 2.72~ 2.90(4H, m), 3.03(2H, t, J=5.7 Hz), 3.5(1H, m), 3.84(3H, s), 4.25(2H, t, J=5.7 Hz), 6.78~7.85(7H, m).

MS(m/z):477(M$^+$), 84.

EXAMPLE 15

[6-Methoxy-2-(3-methylcyclohexyl)benzo[b]thien-3-yl][4-[2-(1-piperidinyl)ethoxy] phenyl]methanone $^1$H-NMR(CDCl$_3$, δ):0.88(3H, d, J=5.3 Hz), 0.94~2.33(15H, m), 2.48~ 2.59(4H, m), 2.81 (2H, t, J=5.9 Hz), 3.1 (1H, m), 3.84(3H, s), 4.19(2H, t, J=5.9 Hz), 6.77~7.85(7H, m).

MS(m/z):491(M$^+$), 98.

EXAMPLE 16

[6-Methoxy-2-(3-methylcyclohexyl)benzo[b]thien-3-yl][4-[2-(1-homopiperidinyl)ethoxy] phenyl]methanone $^1$H-NMR(CDCl$_3$, δ):0.88(3H, d, J=5.5 Hz), 1.00~2.80(17H, m), 2.86~ 3.00(4H, m), 3.08(2H, t, J=5.7 Hz), 3.84(3H, s), 4.23(2H, t, J=5.7 Hz), 6.78~7.85(7H, m).

MS(m/z):505(M$^+$), 112.

EXAMPLE 17

[6-Methoxy-2- (3-methylcyclohexyl)benzo[b]thien-3-yl][4-[2-[1-(3 -methylpiperidinyl)]ethoxy]phenyl]methanone $^1$H-NMR(CDCl$_3$, δ):0.71~0.99(6H, m), 1.00~2.67(16H, m), 2.72~3.15 (5H, m), 3.84(3H, s), 4. 17(2H, t, J=6 Hz), 6.77~7.85(7H, m).

MS(m/z):505(M$^+$), 112.

EXAMPLE 18

(6-Methoxy-2-cyclopentylbenzo[b]thien-3-yl)[4-[3-(1-piperidinyl)propoxy]phenyl]methanone $^1$H-NMR(CDCl$_3$, δ):1.25~2.62(22H, m), 3.3(1H, m), 3.84(3H, s), 4.08 (2H, t, J=6.3 Hz), 6.79~7.87(7H, m).

MS(m/z):477(M$^+$), 98.

EXAMPLE 19

( 6-Methoxy-2-cyclohexylbenzo[b ]thien-3-yl)[4-[3-(diethylamino)propoxy]phenyl]methanone $^1$H-NMR(CDCl$_3$, δ):1.26(6H, t), 1.40~2.36(14H, m), 2.78~3.14(4H, m), 3.84(3H, s), 4.13(2H, t, J=5.8 Hz), 6.77~7.85(7H, m).

MS(m/z):479(M$^+$), 86.

EXAMPLE 20

(6-Methoxy-2-cyclohexylbenzo[b]thien-3-yl)[4-[3-(1-pyrrolidinyl)propoxy]phenyl]methanone $^1$H-NMR(CDCl$_3$, δ):1.15~3.04(23H, m), 3.84(3H, s), 4.11(2H, t, J=6.3 Hz), 6.77~7.85(7H, m).

MS(m/z):477(M$^+$), 84.

EXAMPLE 21

(6-Methoxy-2-cyclohexylbenzo[b ]thien-3-yl)[4-[3-(1-piperidinyl)propoxy]phenyl]methanone $^1$H-NMR(CDCl$_3$, δ):1.12~3.04(18H, m), 2.47(6H, m), 3.0(1H, m), 3.84 (3H, s), 4.09(2H, t, J=6.2 Hz), 6.77~7.88(7H, m).

MS(m/z):491(M$^+$), 98.

EXAMPLE 22

(6-Methoxy-2-cyclohexylbenzo[b]thien-3-yl)[4-[3-(1-homopiperidinyl)propoxy]phenyl]methanone $^1$H-NMR(CDCl$_3$, δ):1.11~3.11(20H, m), 2.85(6H, m), 3.84(3H, s), 4.11 (2H, t, J=6.2 Hz), 6.78~7.85(7H, m).

MS(m/z):505(M$^+$), 112.

EXAMPLE 23

(6-Methoxy-2-cyclohexylbenzo[b]thien-3-yl)[4-[3-[1-(3-methylpiperidinyl)]propoxy] phenyl]methanone $^1$H-NMR(CDCl$_3$, δ):0.87(3H, d, J=5.7 Hz), 1.00~3.13(24H, m), 3.84(3H, s), 4.09(2H, t, J=6.3 Hz), 6.77~7.85(7H, m).

MS(m/z):505(M$^+$), 112.

EXAMPLE 24

(6-Methoxy-2-cyclohexylbenzo[b]thien-3-yl)[4-[3-[1-(4-methylpiperazinyl)]propoxy] phenyl]methanone $^1$H-NMR(CDCl$_3$, δ):1.12~2.29(12H, m), 2.34(3H, s), 2.56(10H, m), 3.84 (3H, s), 4.09(2H, t, J=6.3 Hz), 6.77~7.88(7H, m).

MS(m/z):506(M+), 113.

EXAMPLE 25

(6-Methoxy-2-cyclohexylbenzo[b]thien-3-yl)[4-[3-[2-(1,2,3,4-tetrahydroisoquinolinyl)]propoxyl]phenyl]methanone $^1$H-NMR(CDCl$_3$, δ):1.18~3.67(21H, m), 3.84(3H, s), 4.15(2H, t, J=6.3 Hz), 6.74~8.45(11H, m).

MS(m/z):539(M+), 146.

EXAMPLE 26

(6-Methoxy-2-cycloheptylbenzo[b]thien-3-yl)[4-[3-(1-pyrrolidinyl)propoxy]phenyl]methanone $^1$H-NMR(CDCl$_3$, δ):1.26~3.77(25H, m), 3.84(3H, s), 4.10(2H, t, J=6.3 Hz), 6.78~7.88(7H, m).

MS(m/z):491(M+), 84.

EXAMPLE 27

(6-Methoxy-2-cycloheptylbenzo[b]thien-3-yl)[4-[3-(1-piperidinyl)propoxy]phenyl]methanone $^1$H-NMR(CDCl$_3$, δ):1.26~3.77(27H, m), 3.84(3H, s), 4.08(2H, t, J=6.3 Hz), 6.76~7.88(7H, m).

MS(m/z):505(M+), 98.

EXAMPLE 28

(6-Methoxy-2-cycloheptylbenzo[b]thien-3-yl)[4-[3-(1-homopiperidinyl)propoxy]phenyl]methanone $^1$H-NMR(CDCl$_3$, δ):1.18~3.80(29H, m), 3.84(3H, s), 4.10(2H, t, J=6.3 Hz), 6.78~7.92(7H, m).

MS(m/z):519(M+), 112.

EXAMPLE 29

(6-Methoxy-2-cyclododecylbenzo[b]thien-3-yl)[4-[2-(1-piperidinyl)ethoxy]phenyl]methanone $^1$H-NMR(CDCl$_3$, δ):1.25~1.85(28H, m), 2.62(4H, t, J=5.3 Hz), 2.88(2H, t, J=5.9 Hz), 3.00~3.25(1H, m), 3.76(3H, s), 4.23(2H, t, J=5.9Hz), 6.84~ 7.57(5H, m), 7.79(2H, d, J=8.8 Hz).

MS(m/z):561(M+), 459, 98.

EXAMPLE 30

(6-Methoxy-2-isopropylbenzo[b]thien-3-yl)[4-[2-(1-piperidinyl)ethoxy]phenyl]methanone $^1$H-NMR(CDCl$_3$, δ):1.30(6H, d, J=6.8 Hz), 1.50~1.75(6H, m), 2.57(4H, t, J=7.3 Hz), 2.82(2H, t, J=4.2 Hz), 3.31 (1H, m), 4.06(3H, s), 4.19(2H, t, J=5.9 Hz), 6.76~7.24 (5H, m), 7.80(2H, d, J=9.0 Hz).

MS(m/z):437(M+), 98.

EXAMPLE 31

(6-Methoxy-2-isopropylbenzo[b]thien-3-yl)[4-[2-(1-pyrrolidinyl)ethoxy]phenyl]methanone $^1$H-NMR(CDCl$_3$, δ):1.30(6H, d, J=6.8 Hz), 1.88~2.05(4H, m), 3.00(21H, t, J=5.7 Hz), 3.18(2H, t, J=5.7 Hz), 3.34~3.60(1H, m), 3.84(3H, s), 4.38(2H, t, J=5.3 Hz), 6.79~7.28(5H, m), 7.82(2H, d, J=8.8 Hz).

MS(m/z):423(M+), 84.

EXAMPLE 32

48 mg of sodium hydride was added to a THF solution of 0.2 ml of pyrrolidine, followed by stirring at room temperature for 1 hour. 54 mg of (6-methoxy-2-cyclohexylbenzo[b]thien-3-yl)[4-(2-chloroethoxy)phenyl]methanone was added, followed by reflux with heating for 10 hours. Water was added, the mixture was extracted with ethyl acetate, and the extract was purified by TLC (developing solvent, chloroform:methanol=9:1) to obtain 12 mg of (6-methoxy-2-cyclohexylbenzo[b]thien-3-yl)[4-[2-(1-pyrrolidinyl)ethoxy]phenyl]methanone.

$^1$H-NMR(CDCl$_3$, δ):1.15~2.10(14H, m), 2.67~2.86(4H, m), 3.00(2H, t, J=5.7 Hz), 3.4(1H, m), 3.84(3H, s), 4.23(2H, t, J=5.7 Hz), 6.78~7.86(7H, m).

MS(m/z):463(M+), 84.

The following compounds of Examples 33 and 34 were synthesized in the same manner as in Example 32.

EXAMPLE 33

(6-Methoxy-2-cyclohexylbenzo[b]thien-3-yl)[4-[2-(1-homopiperidinyl)ethoxy]phenyl]methanone $^1$H-NMR(CDCl$_3$, δ):0.83~2.11(18H, m), 2.74~2.95(4H, m), 3.04(2H, t, J=6 Hz), 3.84(3H, s), 4.20(2H, t, J=6 Hz), 6.78~7.88(7H, m).

MS(m/z):491(M+), 112.

EXAMPLE 34

(6-Methoxy-2-cyclohexylbenzo[b]thien-3-yl) [4-[2-(N-morpholinyl)ethoxy]phenyl]methanone $^1$H-NMR(CDCl$_3$, δ):0.85~2.17(10H, m), 2.56~2.66(4H, m), 2.85(2H, t, J=5.7 Hz), 3.0(1H, m), 3.61~3.80(4H, m), 3.84(3H, s), 4.20(2H, t, J=5.7 Hz), 6.77~7.89(7H, m).

MS(m/z):479(M+), 100.

EXAMPLE 35

50 mg of (6-methoxy-2-cyclohexylbenzo[b]thien-3-yl)[4-(2-chloroethoxy)phenyl]methanone was dissolved in 5 ml of DMF, 20 mg of potassium iodide and 0.5 ml of 3-methylpiperidine were added, and the mixture was stirred at about 40° C. for 8 hours, at room temperature for 2 days and then at about 50° C. for 2 hours. The reaction mixture was concentrated under reduced pressure, a saturated aqueous sodium bicarbonate solution was added, and the mixture was extracted with ethyl acetate. The organic layer was washed with saturated saline and then dried over anhydrous magnesium sulfate. The solvent was distilled off, and the residue was purified by TLC (developing solvent, chloroform) to obtain 31 mg of (6-methoxy-2-cyclohexylbenzo[b]thien-3-yl)[4-[2-[1-(3methylpiperidinyl)]ethoxy]phenyl]methanone.

$^1$H-NMR(CDCl$_3$, δ):0.87(3H, d, J=5.7 Hz), 1.01~2.76(17H, m), 2.73~ 3.11(5H, m), 3.84(3H, s), 4.18(2H, t, J=6 Hz), 6.75~7.88(7H, m).

MS(m/z):491(M+), 112.

The following compound of Example 36 was synthesized in the same manner as in Example 35.

EXAMPLE 36

(6-Methoxy-2-cyclohexylbenzo[b]thien-3-yl)[4-[3-(N-morpholinyl)propoxy]phenyl]methanone $^1$H-NMR(CDCl$_3$, δ):1.13~3.04(18H, m), 3.0(1H, m), 3.73(4H, m), 3.84 (3H, s), 4.10(2H, t, J=4.7 Hz), 6.77~7.85(7H, m).

MS(m/z):493(M+), 100.

EXAMPLE 37

The same operations as in Preparation example 6 were carried out using 200 mg of 4-[2-(dimethylamino)ethoxy]benzoic acid in place of 4-(2-chloroethoxy)benzoic acid and 45 mg of 6-methoxy-2-cyclopentylbenzo[b]thiophene in place of 6-methoxy-2-cyclohexylbenzo[b]thiophene, and then purification was carried out by TLC (developing solvent, chloroform:methanol=19:1) to obtain 35 mg of (6-methoxy-2-cyclopentylbenzo[b]thien-3-yl)[4-[2-(dimethylamino)ethoxy] phenyl]methanone.

$^1$H-NMR(CDCl$_3$, δ):1.26~2.29(8H, m), 2.36(6H, s), 2.77(2H, t, J=5.7 Hz), 3.25~3.79(1H, m), 3.84(3H, s), 4.14(2H, t, J=5.7 Hz), 6.79~7.90(7H, m).

MS(m/z):423(M$^+$), 58.

The following compounds of Examples 38 to 58 were synthesized in the same manner as in Example 37.

EXAMPLE 38

(6-Methoxy-2-cyclopentylbenzo[b]thien-3-yl)[4-[2-(diethylamino)ethoxy]phenyl]methanone $^1$H-NMR(CDCl$_3$, δ):1.10(6H, t, J=7.2 Hz), 1.26~2.47(8H, m), 2.70(4H, q), 2.94(2H, t, J=6 Hz), 3.25~3.58(1H, m), 3.84(3H, s), 4.15(2H, t, J=6 Hz), 6.79~7.87(7H, m).

MS(m/z):451(M$^+$), 86.

EXAMPLE 39

(6-Methoxy-2-cyclohexylbenzo[b]thien-3-yl)[4-[2-(dimethylamino)ethoxy]phenyl]methanone $^1$H-NMR(CDCl$_3$, δ):1.18~2.12(10H, m), 2.37(6H, s), 2.6~3.2(3H, m), 3.84(3H, s), 4.16(2H, t, J=5.7 Hz), 6.78~7.85(7H, m).

MS(m/z):437(M$^+$), 58.

EXAMPLE 40

(6-Methoxy-2-cyclohexylbenzo[b]thien-3-yl)[4-[2-(1-piperidinyl)ethoxy]phenyl]methanone $^1$H-NMR(CDCl$_3$, δ):1.15~2.09(10H, m), 2.55~2.66(4H, m), 2.87(2H, t, J=5.8 Hz), 3.0(1H, m), 3.84(3H, s), 4.22(2H, t, J=5.8 Hz), 6.78~7.85(7H, m).

MS(m/z):477(M$^+$), 98.

EXAMPLE 41

(6-Methoxy-2-cycloheptylbenzo[b]thien-3-yl)[4-[2-(dimethylamino)ethoxy]phenyl]methanone $^1$H-NMR(CDCl$_3$, δ):1.26~2.16(12H, m), 2.38(6H, s), 2.80(2H, t, J=5.6 Hz), 2.89~3.73(1H, m), 3.83(3H, s), 4.16(2H, t, J=5.6 Hz), 6.78~7.85(7H, m).

MS(m/z):451(M$^+$) , 58.

EXAMPLE 42

(6-Methoxy-2-cycloheptylbenzo[b]thien-3-yl)[4-[2-(diethylamino)ethoxy]phenyl]methanone $^1$H-NMR(CDCl$_3$, δ):1.15(6H, t, J=7.2 Hz), 1.26~2.16(12H, m), 2.78(4H, q), 3.01(2H, t, J=5.9 Hz), 3.84(3H, s), 4.23(2H, t, J=5.9 Hz), 6.78~7.85 (7H, m).

MS(m/z):479(M$^+$), 86.

EXAMPLE 43

(6-Methoxy-2-cycloheptylbenzo[b]thien-3-yl)[4-[2-(1-piperidinyl)ethoxy]phenyl]methanone $^1$H-NMR(CDCl$_3$, δ):1.25~2.22(18H, m), 3.02~3.31(7H, m), 3.84(3H, s), 4.49~4.60(2H, m), 6.78~7.86(7H, m).

MS(m/z):491(M$^+$), 98.

EXAMPLE 44

[6-Methoxy-2-(3-methylcyclohexyl)benzo[b]thien-3-yl] [4-[2-(dimethylamino)ethoxy]phenyl] methanone $^1$H-NMR(CDCl$_3$, δ):0.85(3H, t, J=6 Hz), 0.94~2.31(9H, m), 2.37(6H, s), 2.78(2H, t, J=5.6 Hz), 3.84(3H, s), 4.15(2H, t, J=5.6 Hz), 6.77~7.85(7H, m).

MS(m/z):451(M$^+$), 58.

EXAMPLE 45

[6-Methoxy-2-(3-methylcyclohexyl)benzo[b]thien-3-yl] [4-[2-(diethylamino)ethoxy]phenyl] methanone $^1$H-NMR(CDCl$_3$, δ):0.87(6H, t), 1.00~2.17(12H, m), 3.22(4H, q), 3.42 (2H, t, J=4.7 Hz), 3.6(1H, m), 3.85(3H, s), 4.60(2H, t, J=4.7 Hz), 6.78~ 7.87(7H, m).

MS(m/z):479(M$^+$), 86.

EXAMPLE 46

[6-Methoxy-2-(4-methylcyclohexyl)benzo[b]thien-3-yl] [4-[2-(1-piperidinyl)ethoxy] phenyl]methanone $^1$H-NMR(CDCl$_3$, δ):0.97(3H, t, J=7.2 Hz), 1.22~2.08(15H, m), 2.51~2.69(4H, m), 2.84(2H, t, J=5.9 Hz), 3.0(1H, m), 3.84(3H, s), 4.21(2H, t, J=5.9 Hz), 6.78~7.88(7H, m).

MS(m/z):491(M$^+$), 98.

EXAMPLE 47

[6-Methoxy-2-(1-cyclooctenyl)benzo[b]thien-3-yl][4-[2-(1-piperidinyl)ethoxy] phenyl]methanone $^1$H-NMR(CDCl$_3$, δ):0.97~2.59(19H, m), 2.65~2.78(4H, m), 2.93(2H, br t), 3.79(3H, s), 4.25(2H, br t), 6.74~8.05(7H, m).

MS(m/z):503(M$^+$), 98.

EXAMPLE 48

(6-Methoxy-2-methylbenzo[b]thien-3-yl)[4-[2-(1-pyrrolidinyl )ethoxy]phenyl]methanone $^1$H-NMR(CD$_3$OD, δ):1.85~2.00(4H, m), 2.43(3H, s), 2.86~3.05(4H, m), 3.18(2H, t, J=5.4 Hz), 3.84(3H, s), 4.29(2H, t, J=5.4 Hz), 6.81~7.85(7H, m).

MS(m/z):395(M$^+$), 84.

EXAMPLE 49

(6-Methoxy-2-chlorobenzo[b]thien-3-yl)[4-[2-(1-pyrrolidinyl)ethoxy]phenyl]methanone $^1$H-NMR(CD$_3$OD, δ):1.83~1.98(4H, m), 2.84~2.91(4H, m), 3.15(2H, t, J= 5.4 Hz), 3.75(3H, s), 4.26(2H, t, J=5.4 Hz), 6.94~7.86(7H, m).

MS(m/z):417, 415.

EXAMPLE 50

(2-Cyclohexylbenzo[b]thien-3-yl)[4-[2-( 1-piperidinyl)ethoxy]phenyl]methanone

¹H-NMR(CDCl₃, δ):1.09~2.22(16H, m), 2.64~2.76(4H, m), 2.95(2H, t, J=5.7 Hz), 3.0(1H, m), 4.30(2H, t, J=5.7 Hz), 6.83~7.89(8H, m).

MS(m/z):447(M⁺), 98.

EXAMPLE 51

(6-Methoxy-2-cyclohexylbenzo[b]thien-3-yl)[4-[2-(1-piperidinylcarbonyl)ethyl]phenyl] methanone ¹H-NMR(CDCl₃, δ):1.14~2.20(16H, m), 2.61~2.74(2H, m), 2.91~3.13 (2H, m), 3.35~3.67(4H, m), 3.84(3H, s), 6.77~7.92(7H, m).

MS(m/z):489(M⁺), 363, 349.

EXAMPLE 52

(6-Methoxy-2-cycloheptylbenzo[b]thien-3-yl)[4-[2-(1-piperidinylcarbonyl)ethyl]phenyl] methanone ¹H-NMR(CDCl₃, δ):1.26~2.06(18H, m), 2.55~2.71(2H, m), 2.94~3.14 (2H, m), 3.30~3.61(4H, m), 3.84(3H, s), 6.77~7.80(7H, m).

MS(m/z):503(M⁺).

EXAMPLE 53

(6-Methoxy-2-cyclohexylbenzo[b]thien-3-yl)[4-[2-(dimethylcarbamoyl)ethyl]phenyl] methanone ¹H-NMR(CDCl₃, δ):1.10~2.17(10H, m), 2.54~2.78(2H, m), 2.95(6H, s), 2.95~3.30(2H, m), 3.84(3H, s), 6.77~7.95(7H, m).

MS(m/z):449(M⁺), 362.

EXAMPLE 54

(6-Methoxy-2-cyclopentylbenzo[b]thien-3-yl)[4-[2-(1-piperidinyl)ethoxy]phenyl] methanone ¹H-NMR(CDCl₃, δ):1.30~2.90(18H, m), 2.97(2H, t, J=6 Hz), 3.35(1H, m), 3.85(3H, s), 4.32(2H, t, J=6 Hz), 6.80~7.40(5H, m), 7.84(2H, d, J=8.8 Hz).

MS(m/z):463(M⁺), 352, 98.

EXAMPLE 55

[6-Methoxy-2-(4-oxocyclohexyl)benzo[b]thien-3-yl][4-[2-(1-piperidinyl)ethoxy] phenyl]methanone ¹H-NMR(CDCl₃, δ):1.30~2.80(18H, m), 2.87(2H, t, J=6 Hz), 3.50(1H, m), 3.85(3H, s), 4.24(2H, t, J=6 Hz), 6.70~7.30(5H, m), 7.81(2H, d, J=9 Hz).

MS(m/z):491(M⁺), 380, 98.

EXAMPLE 56

(6-Methoxy-2-cyclohexylbenzo[b]thien-3-yl)[4-[2-(1-pyrrolidinylcarbonyl)ethyl]phenyl] methanone ¹H-NMR(CDCl₃, δ):1.18~2.05(14H, m), 2.57(2H, t, J=7.7 Hz), 3.08(2H, t, J=7.9 Hz), 2.80~3.60(1H, m), 3.20~3.60(4H, m), 3.84(3H, s), 6.83(1H, dd, J=8.8, 2.4 Hz), 7.15~7.42(4H, m), 7.75(2H, d, J=8.4 Hz).

MS(m/z):475(M⁺).

EXAMPLE 57

[6-Methoxy-2-(2-methylcyclohexyl)benzo[b]thien-3-yl][4-[2-(1-pyrrolidinylcarbonyl)ethyl]phenyl]methanone ¹-NMR(CDCl₃, δ):0.84(3H, d, J=7.3 Hz), 1.25~2.10(13H, m), 2.57(2H, t, J=7.5 Hz), 3.07(2H, t, J=7.5 Hz), 2.90~3.60(5H, m), 3.84(3H, s), 6.82(1 H, dd, J=8.8, 2.4 Hz), 7.11~7.35(4H, m), 7.73(2H, d, J=8.4 Hz).

MS(m/z):489(M⁺).

EXAMPLE 58

(6-Methoxy-2-cycloheptylbenzo[b]thien-3-yl ) [4-2-(1-pyrrolidinylcarbonyl)ethyl]phenyl] methanone ¹H-NMR(CDCl₃, δ):1.26~2.15(16H, m), 2.58(2H, t, J=7.9 Hz), 3.08(2H, t, J=7.9 Hz), 2.90~3.60(1H, m). 3.20~3.53(4H, m), 3.84(3H, s), 6.84(1H, dd, J=8.8, 2.4 Hz), 7.20~7.34(4H, m), 7.75(2H, d, J=8.4 Hz).

MS(m/z):489(M⁺), 273, 72.

EXAMPLE 59

88 mg of chromium trioxide was added to 5 ml of pyridine to give a yellow gruel-like solution, a pyridine solution of 105 mg of (6-methoxy-2-cyclohexylbenzo[b]thien-3-yl)[4-[3-(1-piperidinyl)propyl]phenyl]methanol was added, and the mixture was stirred at room temperature for 1 hour. After addition of ice to the reaction mixture, the mixture was extracted with ethyl acetate and the organic layer was dried over anhydrous magnesium sulfate. The solvent was distilled off, and the resultant crude product was purified by TLC (developing solvent, chloroform:methanol=19:1) to obtain 47 mg of (6-methoxy-2-cyclohexylbenzo[b]thien-3-yl)[4-[3-(1-piperidinyl)propyl]phenyl]methanone.

¹H-NMR(CDCl₃, δ):1.15~2.09(16H, m), 2.30~2.57(6H, m), 2.62~2.96 (4H, m), 3.84(3H, s), 6.78~7.79(7H, m).

MS(m/z):475(M⁺), 98.

The following compounds of Examples 60 to 63 were synthesized in the same manner as in Example 59.

EXAMPLE 60

(6-Methoxy-2-cycloheptylbenzo[b]thien-3-yl)[4-[3-(1-piperidinyl)propyl]phenyl]methanone ¹H-NMR(CDCl₃, δ):1.13~2.19(18H, m), 2.40~3.29(10H, m), 3.85(3H, s), 6.78~7.79(7H, m).

MS(m/z):489(M⁺), 98.

EXAMPLE 61

(6-Methoxy-2-cyclohexylbenzo[b]thien-3-yl)[4-[3-(dimethylamino)propyl]phenyl]methanone ¹H-NMR(CDCl₃, δ):1.05~2.16(12H, m), 2.35(6H, s), 2.35~2.98(4H, m), 3.85(3H, s), 6.78~7.82(7H, m).

MS(m/z):435(M⁺), 58.

EXAMPLE 62

(6-Methoxy-2-cyclohexylbenzo[b]thien-3-yl)[4-[3-(1-pyrrolidinyl)propyl]phenyl]methanone ¹H-NMR(CDCl₃, δ):1.18~2.07(16H, m), 2.54~3.15(9H, m), 3.84(3H, s), 6.78~7.80(7H, m).

MS(m/z):461(M⁺), 84.

EXAMPLE 63

(6-Methoxy-2-cyclohexylbenzo[b]thien-3-yl)[4-[4-(1-pyrrolidinyl)butyl]phenyl]methanone ¹H-NMR(CDCl₃, δ):1.20~2.15(18H, m), 2.40~2.85(8H, m), 2.75~3.15 (1H, m), 3.84(3H, s), 6.83(1H, dd, J=8.8, 2.4 Hz), 7.17~7.40(4H, m), 7.74(2H, d, J=8.1 Hz).

MS(m/z):475(M⁺), 84.

EXAMPLE 64

50 mg of [6-methoxy-2-(4-oxocyclohexyl)benzo[b]thien-3-yl][4-[2-(1-piperidinyl)ethoxy]phenyl]methanone was dissolved in 4 ml of methanol and 0.5 ml of THF, followed by ice cooling, 6 mg of sodium borohydride was added, and the mixture was stirred at 0° C. for 15 minutes. Water was added to the reaction mixture, and the mixture was extracted with ethyl acetate. The organic layer was washed with water and dried over anhydrous sodium sulfate, and then the solvent was distilled off. The resultant crude product was purified by TLC (developing solvent, chloroform:methanol= 19:1) to obtain 32 mg of [6-methoxy-2-(4-hydroxycyclohexyl)benzo[b]thien-3-yl][4-[2-(1-piperidinyl)ethoxy] phenyl]methanone.

$^1$H-NMR(CDCl$_3$, δ):1.10~2.20(14H, m), 2.60~3.00(4H, m), 3.06(2H, t, J=6 Hz), 3. 60(2H, m), 3.85(3H, s), 4.41(2H, t, J=6 Hz), 6.70~7.30(5H, m), 7.80 (2H, d, H=9 Hz).

MS(m/z):493(M$^+$), 382, 323, 98.

EXAMPLE 65

200 mg of aluminum chloride was added to 20 ml of dichloromethane, and while the mixture was stirred at 0° C., 10 ml of a dichloromethane solution of 0.3 ml of oxalyl chloride was added dropwise and the mixture was stirred at 0° C. for 10 minutes. 2 ml of a dichloromethane solution of 100 mg of 4-phenylbutyrylpyrrolidine was added dropwise, and the mixture was stirred at room temperature for 30 minutes. Water was added, the mixture was extracted with dichloromethane, and the organic layer was dried over anhydrous magnesium sulfate and then concentrated. The residue was dissolved in 20 ml of dichloromethane, 100 mg of 6-methoxy-2-cyclohexylbenzo[b]thiophene and 200 mg of aluminum chloride were added, and the mixture was stirred at room temperature for 2 hours. 1 ml of THF, 0.3 ml of 20% hydrochloric acid and 1 ml of water were added to the reaction mixture at 25° C. or less, a saturated aqueous sodium bicarbonate solution was added to make the mixture alkaline, and the mixture was extracted with dichloromethane. The organic layer was dried over anhydrous magnesium sulfate, the solvent was distilled off, and the resultant crude product was purified by TLC (developing solvent, ethyl acetate:n-hexane= 1:5) to obtain 54 mg of (6-methoxy-2-cyclohexylbenzo[b]thien-3-yl)[4-[3-(1-pyrrolidinylcarbonyl)propyl]phenyl]methanone.

MS(m/z):489(M$^+$), 113.

The following compounds of Examples 66–68 were synthesized in the same manner as in Example 65.

EXAMPLE 66

(6-Methoxy-2-cyclohexylbenzo[b]thien-3-yl)[4-[3-(1-piperidinylcarbonyl)propyl]phenyl] methanone $^1$H-NMR(CDCl$_3$, δ):1.17~1.86(16H, m), 1.91~2.15(2H, m), 2.34(2H, t, J=6.8 Hz), 2.76(2H, t, J=7.5 Hz), 3.20~3.65(5H, m), 3.84(3H, s), 6.83(1H, dd, J=9.0, 2.4 Hz), 7.18~7.30(4H, m), 7.75(2H, d, J=8.4 Hz).

MS(m/z):503(M$^+$), 127.

EXAMPLE 67

(6-Methoxy-2-cyclohexylbenzo[b]thien- 3-yl)[4-4-(1-piperidinyl)butyl]phenyl]methanone $^1$H-NMR(CDCl$_3$, δ):1.25~2.05(20H, m), 2.24~2.39(6H, m), 2.69(2H, t, J=7.0 Hz), 2.80~3.10(1H, m), 3.84(3H, s), 6.84(1H, dd, J=9.0, 2.4 Hz), 7.13~ 7.27(5H, m), 7.74(2H, d, J=8.4 Hz).

MS(m/z):489(M$^+$), 98.

EXAMPLE 68

(6-Methoxy-2-cyclohexylbenzo[b]thien-3-yl) [4-[3-(dimethylcarbamoyl)propyl]phenyl]methanone $^1$H-NMR(CDCl$_3$, δ):1.15~1.85(12H, m), 1.90~2.20(2H, m), 2.33(2H, t, J=6.8 Hz), 2.76(2H, t, J=7.7 Hz), 2.95(6H, s), 3.85(3H, s), 6.77~7.80(7H, m).

MS(m/z):463(M$^+$), 87.

EXAMPLE 69

35 mg of (6-methoxy-2-cyclopentylbenzo[b]thien-3-yl) [4-[2-(dimethylamino)ethoxy]phenyl] methanone was dissolved in 5 ml of dichloromethane, 65 mg of aluminum chloride and 0.03 ml of ethanethiol were added, and the mixture was stirred at room temperature for 2 hours. 0.3 ml of THF, 0.075 ml of 20% hydrochloric acid and 0.3 ml of water were added to the reaction mixture, a saturated aqueous sodium bicarbonate solution was added to make the mixture alkaline, and the resultant mixture was extracted with ethyl acetate. The organic layer was dried over anhydrous magnesium sulfate, the solvent was distilled off, and the resultant crude product was purified by TLC (developing solvent, chloroform:methanol=19:1) to obtain 21 mg of (6-hydroxy-2-cyclopentylbenzo[b]thien-3-yl)[4-[2-(dimethylamino)ethoxy]phenyl] methanone.

$^1$H-NMR(CD$_3$OD, δ):1.24~2.27(8H, m), 2.37(6H, s), 2.81(2H, t, J=5.5 Hz), 4.18(2H, t, J=5.5 Hz), 6.68~7.87(7H, m).

MS(m/z):409(M$^+$), 58.

The following compounds of Examples 70 to 132 were synthesized in the same manner as in Example 69.

EXAMPLE 70

(6-Hydroxy-2-cyclopentylbenzo[b]thien-3-yl)[4-[2-(diethylamino)ethoxy]phenyl]methanone $^1$H-NMR(CD$_3$OD, δ):1.06(6H, t, J=7.2 Hz), 1.20~2.21 (8H, m), 2.64(4H, q), 2.89(2H, t, J=5.7 Hz), 4.12(2H, t, J=5.7 Hz), 6.68~7.84(7H, m).

MS(m/z):437(M$^+$), 86.

EXAMPLE 71

(6-Hydroxy-2-cyclopentylbenzo[b]thien-3-yl)[4-[2-(1-pyrrolidinyl)ethoxy]phenyl]methanone $^1$H-NMR(CD$_3$OD, δ):1.23~2.15(12H, m), 2.62~2.79(4H, m), 2.99(2H, t, J=5.5 Hz), 4.22(2H, t, J=5.5 Hz), 6.69~7.84(7H, m).

MS(m/z):435(M$^+$), 84.

EXAMPLE 72

(6-Hydroxy-2-cyclopentylbenzo[b]thien-3-yl)[4-[2-(1-homopiperidinyl)ethoxy]phenyl]methanone $^1$H-NMR(CD$_3$OD, δ):1.26~2.15(16H, m), 2.83~2.91(4H, m), 3.05(2H, t, J=5.6 Hz), 4.22(2H, t, J=5.6 Hz), 6.68~7.84(7H, m).

MS(m/z):463(M$^+$), 112.

EXAMPLE 73

(6-Hydroxy-2-cyclopentylbenzo[b]thien-3-yl)[4-[2-[1-(3-methylpiperidinyl)]ethoxy] phenyl]methanone $^1$H-NMR(CD$_3$OD, δ):0.89(3H, d, J=5.7 Hz), 1.29~2.15(15H, m), 2.81~ 3.04(5H, m), 4.24(2H, t, J=5.6 Hz), 6.69~7.84(7H, m).

MS(m/z):463(M$^+$), 112.

EXAMPLE 74

(6-Hydroxy-2-cyclohexylbenzo[b]thien-3-yl)[4-[2-(dimethylamino)ethoxy]phenyl]methanone $^1$H-NMR(CD$_3$OD, δ):1.09~2.29(10H, m), 2.36(6H, s), 2.81(2H, t, J=5.5 Hz), 4.19(2H, t, J=5.5 Hz), 6.68~7.83(7H, m).

MS(m/z):423(M$^+$), 58.

EXAMPLE 75

(6-Hydroxy-2-cyclohexylbenzo[b]thien-3-yl)[4-[2-(diethylamino)ethoxy]phenyl]methanone $^1$H-NMR(CD$_3$OD, δ):1.11(6H, t, J=7.2 Hz), 1.22~1.94(10H, m), 2.72(4H, q), 2.98(2H, t, J=5.6 Hz), 4.21 (2H, t, J=5.6 Hz), 6.69~7.8.3(7H, m).

MS(m/z):451(M$^+$), 86.

EXAMPLE 76

(6-Hydroxy-2-cyclohexylbenzo[b]thien-3-yl)[4-[2-(1-pyrrolidinyl)ethoxy]phenyl]methanone $^1$H-NMR(CD$_3$OD, δ):1.11~2.03(14H, m), 2.78~2.99(4H, m), 3.10(2H, t, J=5.4 Hz), 4.27 (2H, t, J=5.4 Hz), 6.68~7.86(7H, m).

MS(m/z):449(M$^+$), 84.

EXAMPLE 77

(6-Hydroxy-2-cyclohexylbenzo[b]thien-3-yl)[4-[2-(1-piperidinyl)ethoxy]phenyl]methanone $^1$H-NMR(CD$_3$OD, δ):1.15~2.14(16H, m), 2.50~2.61(4H, m), 2.80(2H, t, J=5.5 Hz), 3.0(1H, m), 4.18(2H, t, J=5.5 Hz), 6.67~7.80(7H, m).

MS(m/z):463(M$^+$), 98.

EXAMPLE 78

(6-Hydroxy-2-cyclohexylbenzo[b]thien-3-yl)[4-[2-(1-homopiperidinyl)ethoxy]phenyl]methanone MS(m/z):477(M$^+$), 112.

EXAMPLE 79

(6-Hydroxy-2-cyclohexylbenzo[b]thien-3-yl)[4-[2-[1-(3-methylpiperidinyl)]ethoxy] phenyl]methanone $^1$H-NMR(CD$_3$OD, δ):0.87(3H, d, J=5.7 Hz), 1.01~2.26(17H, m), 2.73~ 3.12(5H, m), 4.20(2H, t, J=5.6 Hz), 6.68~7.84(7H, m).

MS(m/z):477(M$^+$), 112.

EXAMPLE 80

(6-Hydroxy-2-cyclohexylbenzo[b]thien-3-yl)[4-[2-(N-morpholinyl)ethoxy]phenyl]methanone $^1$H-NMR(CD$_3$OD, δ):0.89~2.06(10H, m), 2.59(4H, br t), 2.82(2H, t, J=5.5 Hz), 3.70(4H, br t), 4.23(2H, t, J=5.5 Hz), 6.69~7.85(7H, m).

MS(m/z):465(M$^+$), 100.

EXAMPLE 81

(6-Hydroxy-2-cyclohexylbenzo[b]thien-3-yl)[4-[2-[1-(4-methylpiperazinyl)]ethoxy] phenyl]methanone $^1$H-NMR(CD$_3$OD, δ):0.89~2.08(10H, m), 2.58(3H, s), 2.61~3.00(10H, m), 4.23(2H, t, J=5.4 Hz), 6.68~7.83(7H, m).

MS(m/z):478(M$^+$), 113.

EXAMPLE 82

(6-Hydroxy-2-cyclohexylbenzo[b]thien-3-yl)[4-[2-[2-(1,2,3,4-tetrahydroisoquinolinyl)] ethoxy]phenyl]methanone $^1$H-NMR(CD$_3$OD, δ):1.08~2.17(10H, m), 2.80~3.04(9H, m), 3.75(2H, s), 4.28(2H, t, J=5.6 Hz), 6.68~7.82(11H, m).

MS(m/z):511(M$^+$), 146.

EXAMPLE 83

(6-Hydroxy-2-cyclohexylbenzo[b]thien-3-yl)[4-[2-[1-(4-hydroxypiperidinyl)]ethoxy] phenyl]methanone $^1$H-NMR(CD$_3$OD, δ):1.08~3.08(21H, m), 3.56~3.70(1H, m), 4.22(2H, t, J=5.5 Hz), 6.69~7.86(7H, m).

MS(m/z):479(M$^+$), 114.

EXAMPLE 84

(6-Hydroxy-2-cycloheptylbenzo[b]thien-3-yl)[4-[2-(dimethylamino)ethoxy]phenyl]methanone $^1$H-NMR(CD$_3$OD, δ):1.28~2.15(12H, m), 2.39(6H, s), 2.85(2H, t, J=5.5 Hz), 4.20(2H, t, J=5.5 Hz), 6.68~7.83(7H, m).

MS(m/z):437(M$^+$), 58.

EXAMPLE 85

(6-Hydroxy-2-cycloheptylbenzo[b]thien-3-yl)[4-[2-(diethylamino)ethoxy]phenyl]methanone $^1$H-NMR(CD$_3$OD, δ):1.11(6H, t, J=7.2 Hz), 1.22~1.93(12H, m), 2.71(4H, q), 2.97 (2H, t, J=5.6 Hz), 4.20(2H, t, J=5.6 Hz), 6.79~7.83(7H, m).

MS(m/z):465(M$^+$), 86.

EXAMPLE 86

(6-Hydroxy-2-cycloheptylbenzo[b]thien-3-yl)[4-[2-(1-pyrrolidinyl)ethoxy]phenyl]methanone $^1$H-NMR(CD$_3$OD, δ):1.17~2.07(16H, m), 2.71~2.99(4H, m), 3.08(2H, t, J=5.5 Hz), 4.26(2H, t, J=5.5 Hz), 6.69~7.86(7H, m).

MS(m/z):463(M$^+$), 84.

EXAMPLE 87

(6-Hydroxy-2-cycloheptylbenzo[b]thien-3-yl)[4-[2-(1-piperidinyl)ethoxy]phenyl]methanone $^1$H-NMR(CD$_3$OD, δ):1.24~2.07(18H, m), 2.53~2.68(4H, m), 2.83(2H, t, J=5.6 Hz), 4.23(2H, t, J=5.6 Hz), 6.69~7.83(7H, m).

MS(m/z):477(M$^+$), 98.

EXAMPLE 88

(6-Hydroxy-2-cycloheptylbenzo[b]thien-3-yl)[4-[2-(1-homopiperidinyl)ethoxy]phenyl]methanone ¹H-NMR(CD₃OD, δ):1.17~2.17(20H, m), 2.75~2.95(4H, m), 3.05(2H, t, J=5.6 Hz), 4.22(2H, t, H=5.6 Hz), 6.68~7.85(7H, m).

MS(m/z):491(M⁺), 112.

EXAMPLE 89

(6-Hydroxy-2-cycloheptylbenzo[b]thien-3-yl)[4-[2-[1-(3-methylpiperidinyl)]ethoxy] phenyl]methanone ¹H-NMR(CD₃OD, δ):0.83(3H, d, J=5.7 Hz), 1.53~2.06(18H, m), 2.77~3.08(5H, m), 4.21(2H, t, J=5.6 Hz), 6.67~7.82(7H, m).

MS(m/z):491(M⁺), 112.

EXAMPLE 90

[6-Hydroxy-2-(2-methylcyclohexyl)benzo[b]thien-3-yl][4-[2-(1-pyrrolidinyl)ethoxy] phenyl]methanone ¹H-NMR(CD₃OD, δ):0.83(3H, d, J=7.0 Hz), 1.28~2.05(13H, m), 2.68~2.86(4H, m), 3.01(2H, t, J=5.5 Hz), 4.24(2H, t, J=5.5 Hz), 6.69~7.84(7H, m).

MS(m/z):463(M⁺), 84.

EXAMPLE 91

[6-Hydroxy-2-(2-methylcyclohexyl)benzo[b]thien-3-yl][4-[2-(1-piperidinyl)ethoxy] phenyl]methanone ¹H-NMR(CD₃OD, δ):0.83(3H, d, J=7.0 Hz), 1.23~2.15(15H, m), 2.60~2.71(4H, m), 2.90(2H, t, J=5.5 Hz), 4.24(2H, t, J=5.5 Hz), 6.68~7.83(7H, m).

MS(m/z):477(M⁺), 98.

EXAMPLE 92

[6-Hydroxy-2-(2-methylcyclohexyl)benzo[b]thien-3-yl][4-[2-(1-homopiperidinyl)ethoxy] phenyl]methanone ¹H-NMR(CD₃OD, δ):0.84(3H, d, J=7.0 Hz), 1.12~2.03(17H, m), 2.85~2.95(4H, m), 3.07(2H, t, J=5.7 Hz), 4.24(2H, t, J=5.7 Hz), 6.69~7.84(7H, m).

MS(m/z):491(M⁺), 112.

EXAMPLE 93

[6-Hydroxy-2-(3-methylcyclohexyl)benzo[b]thien-3-yl][4-[2-(dimethylamino)ethoxy]phenyl] methanone ¹H-NMR(CD₃OD, δ):0.87(3H, d, J=6.6 Hz), 1.03~2.00(9H, m), 2.39(6H, s), 2.85(2H, t, J=5.5 Hz), 4.20(2H, t, J=5.5 Hz), 6.68~7.83(7H, m).

MS(m/z):437(M⁺), 58.

EXAMPLE 94

[6-Hydroxy-2-(3-methylcyclohexyl)benzo[b]thien-3-yl][4-[2-(diethylamino)ethoxy]phenyl] methanone ¹H-NMR(CD₃OD, δ):0.88(3H, d, J=7.0 Hz), 1.18(6H, t), 1.26~2.15(9H, m), 2.82(4H, q), 3.08(2H, t, J=5.5 Hz), 4.24(2H, t, J=5.5 Hz), 6.69~7.89(7 H, m).

MS(m/z):465(M⁺), 86.

EXAMPLE 95

[6-Hydroxy-2-(3-methylcyclohexyl)benzo[b]thien-3-yl][4-[2-(1-pyrrolidinyl)ethoxy] phenyl]methanone ¹H-NMR(CD₃OD, δ):0.88(3H, d, J=5.5 Hz), 1.17~1.96(13H, m), 2.76~2.89(4H, m), 3.08(2H, t, J=5.4 Hz), 4.26(2H, t, J=5.4 Hz), 6.78~7.84(7H, m).

MS(m/z):463(M⁺), 84.

EXAMPLE 96

[6-Hydroxy-2-(3-methylcyclohexyl)benzo[b]thien-3-yl][4-[2-(1-piperidinyl)ethoxy] phenyl]methanone ¹H-NMR(CD₃OD, δ):0.88(3H, d, J=5.9 Hz), 1.16~2.03(21H, m), 3.58(2H, t, J=4.6 Hz), 4.49(2H, t, J=4.6 Hz), 6.77~7.86(7H, m).

MS(m/z):477(M⁺), 98.

EXAMPLE 97

[6-Hydroxy-2-(3-methylcyclohexyl)benzo[b]thien-3-yl][4-[2-(1-homopiperidinyl)ethoxy] phenyl]methanone ¹H-NMR(CD₃OD, δ):0.88(3H, d, J=5.5 Hz), 1.03~1.91(17H, m), 2.89~3.02(4H, m), 3.11(2H, t, J=5.5 Hz), 4.25(2H, t, J=5.5 Hz), 6.69~7.83(7H, m).

MS(m/z):491(M⁺), 112.

EXAMPLE 98

[6-Hydroxy-2-(3-methylcyclohexyl)benzo[b]thien-3-yl][4-[2-[1-(3-methylpiperidinyl)]ethoxy]phenyl]methanone ¹H-NMR(CD₃OD, δ):0.84~1.00(6H, m), 1.00~3.20(20H, m), 4.30(2H, t, J=5.5 Hz), 6.68~7.83(7H, m).

MS(m/z):4.91(M⁺), 112.

EXAMPLE 99

[6-Hydroxy-2-(4-methylcyclohexyl)benzo[b]thien-3-yl][4-[2-(1-piperidinyl)ethoxy] phenyl]methanone ¹H-NMR(CD₃OD, δ):0.94(3H, d, J=7.7 Hz), 1.02~1.94(9H, m), 2.59~2.75(4H, m), 2.89(2H, t, J=5.5 Hz), 4.25(2H, t, J=5.5 Hz), 6.69~7.86(7H, m).

MS(m/z):477(M⁺), 98.

EXAMPLE 100

[6-Hydroxy-2-(1-cyclooctenyl)benzo[b]thien-3-yl][4-[2-(1-piperidinyl)ethoxy] phenyl]methanone ¹H-NMR(CD₃OD, δ):0.84~1.88(19H, m), 2.57~2.84(6H, m), 4.18(2H, t), 6.77~7.94(7H, m).

MS(m/z):489(M⁺), 98.

EXAMPLE 101

(6-Hydroxy-2-methylbenzo[b]thien-3-yl)[4-[2-(1-pyrrolidinyl)ethoxy]phenyl]methanone ¹H-NMR(CD₃OD, δ):1.77~1.99(4H, m), 2.40(3H, s), 2.62~2.82(4H, m), 2.96(2H, t, J=5.5 Hz), 4.23(2H, t, J=5.5 Hz), 6.71~7.87(7H, m).

MS(m/z):381(M⁺), 84.

EXAMPLE 102

(6-Hydroxy-2-cyclopentylbenzo[b]thien-3-yl)[4-[3-(1-piperidinyl)propoxy]phenyl]methanone ¹H-NMR(CD₃OD, δ):1.25~2.17(16H, m), 2.46~2.66(6H, m), 4.09(2H, t, J=6 Hz), 6.68~7.82(7H, m).

EXAMPLE 103

(6-Hydroxy-2-cyclohexylbenzo[b]thien-3-yl)[4-[3-(diethylamino)propoxy]phenyl]methanone ¹H-NMR(CD₃OD, δ):1.07~2.13(18H, m), 2.68~2.97(7H, m), 4.15(2H, t, J=5.9 Hz), 6.71~7.83(7H, m).

MS(m/z):465(M⁺), 86.

EXAMPLE 104

(6-Hydroxy-2-cyclohexylbenzo[b]thien-3-yl)[4-[3-(1-pyrrolidinyl)propoxy]phenyl]methanone $^1$H-NMR(CD$_3$OD, δ):1.11~2.22(16H, m), 2.67~3.06(7H, m), 4.13(2H, t, J=5.81 Hz), 6.68~7.85(7H, m).
MS(m/z):463(M$^+$), 84.

EXAMPLE 105

(6-Hydroxy-2-cyclohexylbenzo[b]thien-3-yl)[4-[3-(1-piperidinyl)propoxy]phenyl]methanone $^1$H-NMR(CD$_3$OD, δ):1.16~2.13(18H, m), 2.58~2.89(7H, m), 4.11(2H, t, J=6 Hz), 6.68~7.81 (7H, m).
MS(m/z):477(M$^+$), 98.

EXAMPLE 106

(6-Hydroxy-2-cyclohexylbenzo[b]thien-3-yl)[4-[3-(1-homopiperidinyl)propoxy]phenyl]methanone $^1$H-NMR(CD$_3$OD, δ):1.17~3.38(27H, m), 4.20(2H, t, J=5.6 Hz), 6.78~7.83(7H, m).
MS(m/z):491(M$^+$), 112.

EXAMPLE 107

(6-Hydroxy-2-cyclohexylbenzo[b]thien-3-yl)[4-[3-[1-(3-methylpiperidinyl)]propoxy]phenyl]methanone $^1$-NMR(CD$_3$OD, δ):0.95(3H, d, J=5.9 Hz), 1.06~3.34(24H, m), 4.15(2H, t, J=5.81 Hz), 6.68~7.82(7H, m).
MS(m/z):491(M$^+$), 112.

EXAMPLE 108

(6-Hydroxy-2-cyclohexylbenzo[b]thien-3-yl)[4-[3-(N-morpholinyl)propoxy]phenyl]methanone $^1$H-NMR(CD$_3$OD, δ):1.09~2.13(12H, m), 2.43~2.91(7H, m), 3.69(4H, br t), 4.12(2H, t, J=6 Hz), 6.68]7.84(7H, m).
MS(m/z):479(M$^+$), 100.

EXAMPLE 109

(6-Hydroxy-2-cyclohexylbenzo[b]thien-3-yl)[4-[3-[1-(4-methylpiperazinyl)]propoxy] phenyl]methanone $^1$H-NMR(CD$_3$OD, δ):1.14~2.10(12H, m), 2.52(3H, s), 2.57~2.90(11H, m), 4.17(2H, t, J=6 Hz), 6.78~7.82(7H, m).
MS(m/z):492(M$^+$), 113.

EXAMPLE 110

(6-Hydroxy-2-cyclohexylbenzo[b]thien-3-yl)[4-[3-[2-(1,2,3,4-tetrahydroisoquinolinyl)] propoxy]phenyl]methanone
MS (m/z):525(M$^+$), 146.

EXAMPLE 111

(6-Hydroxy-2-cycloheptylbenzo[b]thien-3-yl)[4-3-(1-pyrrolidinyl)propoxy]phenyl]methanone $^1$H-NMR(CD$_3$OD, δ):1.25~2.24(18H, m), 2.51~3.16(7H, m), 4.11(2H, t, J=5.9 Hz), 6.68~7.84 (7H, m).
MS(m/z):477(M$^+$), 84.

EXAMPLE 112

(6-Hydroxy-2-cycloheptylbenzo[b]thien-3-yl)[4-[3-(1-piperidinyl)propoxy]phenyl]methanone $^1$H-NMR(CD$_3$OD, δ):1.17~2.17(20H, m), 2.42~2.75(7H, m), 4.09(2H, t, J=5.9 Hz), 6.68~7.83(7H, m).
MS(m/z):491(M$^+$), 98.

EXAMPLE 113

(6-Hydroxy-2-cycloheptylbenzo[b]thien-3-yl)[4-[3-(1-homopiperidinyl)propoxy]phenyl]methanone $^1$H-NMR(CD$_3$OD, δ):1.24~2.17(22H, m), 2.71~3.00(7H, m), 4.11(2H, t, J=5.9 Hz), 6.67~7.81 (7H, m).
MS(m/z):505(M$^+$), 112.

EXAMPLE 114

(6-Hydroxy-2-cyclohexylbenzo[b]thien-3-yl)[4-[2-(1-piperidinylcarbonyl)ethyl]phenyl] methanone $^1$H-NMR(CD$_3$OD, δ):1.15~1.94(16H, m), 2.73~3.03(4H, m), 3.27~3.64 (4H, m), 6.68~7.77(7H, m).
MS(m/z):475(M$^+$), 348, 335.

EXAMPLE 115

(6-Hydroxy-2-cyclohexylbenzo[b]thien-3-yl)[4-[3-(1-piperidinyl)propyl]phenyl]methanone $^1$H-NMR(CDCl$_3$, δ):1.10~2.17(16H, m), 2.33~2.98(10H, m), 6.64~7.74(7H, m).
MS(m/z):461(M$^+$), 98.

EXAMPLE 116

(6-Hydroxy-2-cycloheptylbenzo[b]thien-3-yl)[4-[2-(1-piperidinylcarbonyl)ethyl]phenyl] methanone $^1$H-NMR(CD$_3$OD, δ):1.11~2.17(18H, m), 2.56~2.80(2H, m), 2.92~3.20 (2H, m), 3.27~3.60(4H, m), 6.67~7.75(7H, m).
MS(m/z):489(M$^+$), 363,349.

EXAMPLE 117

(6-Hydroxy-2-cycloheptylbenzo[b]thien-3-yl)[4-[3-(1-piperidinyl)propyl]phenyl]methanone $^1$H-NMR(CD$_3$OD, δ):1.22~2.15(18H, m), 2.32~2.48(4H, m), 2.65~2.82 (2H, m), 2.96~3.10(4H, m), 6.69~7.77(7H, m).
MS(m/z):475(M$^+$), 98.

EXAMPLE 118

(6-Hydroxy-2-cyclohexylbenzo[b]thien-3-yl)[4-[3-(dimethylamino)propyl]phenyl]methanone $^1$H-NMR(CD$_3$OD, δ):1.13~2.12(12H, m), 2.72~3.12(4H, m), 2.77(6H, s), 6.77~7.81 (7H, m).
MS(m/z):421(M$^+$), 58.

EXAMPLE 119

(6-Hydroxy-2-cyclopentylbenzo[b]thien-3-yl)[4-[2-(1-piperidinyl)ethoxy]phenyl]methanone $^1$H-NMR(CDCl$_3$, δ):1.30~2.30(14H, m), 2.60(4H, m), 2.85(2H, t, J=6 Hz), 3.30(1H, m), 4.18(2H, t, J=6 Hz), 6.60~7.30(5H, m), 7.75(2H, d, J=8.8Hz).
MS(m/z):449(M$^+$), 98.

EXAMPLE 120

[6-Hydroxy-2-(4-hydroxycyclohexyl)benzo[b]-thien-3-yl][4-[2-(1-piperidinyl)ethoxy] phenyl]methanone ¹H-NMR(CD₃OD, δ):1.10~2.20(14H, m), 2.60~2.90(4H, m), 2.97(2H, t, J=6 Hz), 3.55(2H, m), 4.27(2H, t, J=6 Hz), 6.60~7.30(5H, m), 7.78(2H, 8.8 Hz).

MS(m/z):479(M⁺), 368, 309, 98.

EXAMPLE 121

(6-Hydroxy-2-cyclododecylbenzo[b]thien-3-yl)[4-[2-(1-piperidinyl)ethoxy]phenyl]methanone ¹H-NMR(CDCl₃, δ):1.15~1.85(28H, m), 2.65(4H, t, J=4.8 Hz), 2.92(2H, t, J=5.5 Hz), 3.00~3.40(1H, m), 4.29(2H, t, J=5.9 Hz), 6.87~7.86(8H, MS(m/z):547(M⁺), 98.

EXAMPLE 122

(6-Hydroxy-2-isopropylbenzo[b]thien-3-yl)[4-[2-(1-piperidinyl)ethoxy]phenyl]methanone ¹H-NMR(CDCl₃, δ):1.28(6H, d, J=6.8 Hz), 1.45~1.84(6H, m), 2.61(4H, t, J=2.6 Hz), 2.85(2H, t, J=5.7 Hz), 3.31(1H, m), 4.19(2H, t, J=5.5 Hz), 4.5~5.2(1H, br s), 6.65~7.24(5H, m), 7.85(2H, d, J=8.8 Hz).

MS(m/z):423(M⁺), 98.

EXAMPLE 123

(6-Hydroxy-2-isopropylbenzo[b]thien-3-yl)[4-[2-(1-pyrrolidinyl)ethoxy]phenyl]methanone ¹H-NMR(CDCl₃, δ):1.27(6H, d, J=6.8 Hz), 1.80~2.05(4H, m), 2.91(4H, t, J=3.0 Hz), 3.11(2H, t, J=5.1Hz), 3.00~3.44(1H, m), 4.27(2H, t, J=5.3 Hz), 4.0~4.5(1H, br s), 6.67~7.76(7H, m).

MS(m/z):409(M⁺), 84.

EXAMPLE 124

(6-Hydroxy-2-cyclohexylbenzo[b]thien-3-yl)[4-[2-(1-pyrrolidinylcarbonyl)ethyl]phenyl] methanone ¹H-NMR(CDCl₃, δ):1.20~2.04(14H, m), 2.59(2H, t, J=7.9 Hz), 3.07(2H, t, J=7.9 Hz), 2.80~3.60(1H, m), 3.25~3.55(4H, m), 6.72~7.78(8H, m).

MS(m/z):461(M⁺), 72.

EXAMPLE 125

(6-Hydroxy-2-cyclohexylbenzo[b]thien-3-yl)[4-[3-(1-pyrrolidinyl)propyl]phenyl]methanone ¹H-NMR(CDCl₃, δ):1.10~2.20(16H, m), 2.60~3.00(9H, m), 6.69~7.74 (7H, m).

MS(m/z):447(M⁺), 84.

EXAMPLE 126

[6-Hydroxy-2-(2-methylcyclohexyl)benzo[b]thien-3-yl][4-[2-(1-pyrrolidinylcarbonyl)ethyl)phenyl]methanone ¹H-NMR(CDCl₃, δ):0.82(3H, d, J=7.0 Hz), 1.10~2.20(13H, m), 2.59(2H, t, J=7.7 Hz), 2.90~3.80(1H, m), 3.07(2H, t, J=7.9 Hz), 3.40(4H, t, J=6.6 Hz), 6.78(1H, dd, J=8.6, 2.4 Hz), 7.03~7.31(4H, m), 7.72(2H, d, J=8.4 Hz).

MS(m/z):475(M⁺), 72.

EXAMPLE 127

(6-Hydroxy-2-cycloheptylbenzo[b]thien-3-yl)[4-[2-(1-pyrrolidinylcarbonyl)ethyl]phenyl] methanone ¹H-NMR(CDCl₃, δ):1.20~2.15(16H, m), 2.59(2H, t, J=7.9 Hz), 2.80~3.70(1H, m), 3.07(2H, t, J=7.5 Hz), 3.20~3.60(4H, m), 6.77(1H, dd, J=8.8, 2.4 Hz), 7.11~7.32(5H, m), 7.74 (2H, d, J=8.4 Hz).

MS(m/z):475(M⁺), 259, 72.

EXAMPLE 128

(6-Hydroxy-2-cyclohexylbenzo[b]thien-3-yl)[4-[3-(1-pyrrolidinylcarbonyl)propyl]phenyl] methanone ¹H-NMR(CDCl₃, δ):1.50~2.17(14H, m), 2.24(2H, t, J=6.4 Hz), 2.74(2H, t, J=7.5 Hz), 3.28~3.55(5H, m), 6.78(1H, dd, J=8.8, 2.4 Hz), 7.09~7.26(5H, m), 7.72(2H, d, J=8.4 Hz).

MS(m/z):475(M⁺), 113.

EXAMPLE 129

(6-Hydroxy-2-cyclohexylbenzo[b]thien-3-yl)[4-[4-(1-pyrrolidinyl)butyl]phenyl]methanone ¹H-NMR(CDCl₃, δ):1.13~2.08(18H, m), 2.62~2.94(8H, m), 3.10~3.40 (1H, m), 6.73(1H, dd, J=8.6, 2.2 Hz), 6.82~7.23(5H, m), 7.67(2H, d, J=8.1 Hz).

MS(m/z):461(M⁺), 84.

EXAMPLE 130

(6-Hydroxy-2-cyclohexylbenzo[b]thien-3-yl)[4-[3-(1-piperidinylcarbonyl)propyl]phenyl] methanone ¹H-NMR(CDCl₃, δ):1.12~1.85(16H, m), 1.90~2.14(2H, m), 2.37(2H, t, J=6.8 Hz), 2.74(2H, t, J=7.9 Hz), 3.30~3.60(5H, m), 6.77(1H, dd, J=8.8, 2.4 Hz), 7.10~7.26(5H, m), 7.73(2H, d, J=8.1 Hz).

MS(m/z):489(M⁺), 127.

EXAMPLE 131

(6-Hydroxy-2-cyclohexylbenzo[b]thien-3-yl)[4-[4-(1-piperidinyl)butyl]phenyl]methanone ¹H-NMR(CDCl₃, δ):1.17~2.03(20H, m), 2.30~2.75(6H, m), 2.80~3.20 (1H, m), 3.50~4.10(2H, m), 6.71(1H, dd, J=8.8, 2.4 Hz), 7.07~7.22(5H, m), 7.70(2H, d, J=8.4 Hz).

MS(m/z):475(M⁺), 98.

EXAMPLE 132

(6-Hydroxy-2-cyclohexylbenzo[b]thien-3-yl)[4-[3-(dimethylcarbamoyl)propyl]phenyl]methanone ¹H-NMR(CDCl₃, δ):1.16~1.85(12H, m), 1.90~2.15(2H, m); 2.35(2H, t, J=7.3 Hz), 2.75(2H, t, J=7.7 Hz). 2.5~3.1 (1H, m), 2.96(6H, s), 6.69~7.79 (8H, m).

MS(m/z):449(M⁺), 87.

EXAMPLE 133

27 mg of (6-hydroxy-2-cyclohexylbenzo[b]thien-3-yl)[4-[2-(1-piperidinyl)ethoxy]phenyl] methanone was dissolved in 1 ml of pyridine, 0.1 ml of benzoyl chloride was added, and the mixture was stirred at room temperature for 1 hour. After addition of ice, the reaction mixture was stirred for 1 hour and extracted with ethyl acetate. The organic layer was dried over anhydrous magnesium sulfate, the solvent was distilled off, and the resultant crude product was purified by TLC (developing solvent, chloroform:methanol=9:1) to obtain 37 mg of (6-benzoyloxy-2-cyclohexylbenzo[b]thien-3-yl)[4-[2-(1-piperidinyl)ethoxy]phenyl]methanone.

¹H-NMR(CD₃OD, δ):1.17~1.96(16H, m), 2.62~2.73(4H, m), 2.92(2H, t, J=5.6 Hz), 4.25(2H, t, J=5.6 Hz), 6.98~8.22(12H, m).

MS(m/z):567(M⁺), 98.

The following compounds of Examples 134 to 138 were synthesized in the same manner as in Example 133.

EXAMPLE 134

(6-Dimethylcarbamoyloxy-2-cyclohexylbenzo[b]thien-3-yl)[4-[2-(1-piperidinyl)ethoxy]phenyl] methanone ¹H-NMR(CDCl₃δ):1.13~2.11(16H, m), 2.54~2.65(4H, m), 2.86(2H, t, J=5.7 Hz), 3.02(6H, s), 4.22(2H, t, J=5.7 Hz), 6.83~7.88(7H, m).

MS(m/z):534(M⁺), 98, 72.

EXAMPLE 135

(6-Benzoyloxy-2-cyclohexylbenzo[b]thien-3-yl) [4-[2-(1-pyrrolidinyl)ethoxy]phenyl]methanone ¹H-NMR(CD₃OD, δ):1.17~2.16(14H, m), 3.27~3.50(4H, m), 3.59(2H, t), 4.43(2H, t), 7.03~8.24(12H, m).

MS(m/z):553(M⁺), 84.

EXAMPLE 136

(6-Benzoyloxy-2-cycloheptylbenzo[b]thien-3-yl) [4-[3-(1-piperidinyl)propoxy]phenyl]methanone ¹H-NMR(CDCl₃, δ):1.17~2.62(20H, m), 3.02~3.23(6H, m), 4.12(2H, m), 6.71~8.27(12H, m).

MS(m/z):595(M⁺), 98.

EXAMPLE 137

(6-Benzoyloxy-2-cycloheptylbenzo[b]thien-3-yl) [4-[3-(1-homopiperidinyl)propoxy]phenyl]methanone ¹H-NMR(CDCl₃, δ):1.26~2.49(22H, m), 3.04~3.44(6H, m), 4.11(2H, m), 6.81~8.27(12H, m).

MS(m/z):609(M⁺), 112.

EXAMPLE 138

(6-Benzoyloxy-2-cycloheptylbenzo[b]thien-3-yl) [4-[3-(1-pyrrolidinyl)propoxy]phenyl]methanone ¹H-NMR(CDCl₃, δ):1.21~2.63(18H, m), 3.20~3.39(4H, m), 4.09~4.22 (2H, m), 6.83~8.27(12H, m).

MS(m/z):581(M⁺), 84.

EXAMPLE 139

A mixture of 10 mg of [6-hydroxy-2-(4-hydroxycyclohexyl)benzo[b]thien-3-yl][4-[2-( 1-piperidinyl)ethoxy]phenyl]methanone, 0.5 ml of acetic anhydride and 0.5 ml of pyridine was stirred at room temperature for 18 hours. After addition of cold water, the reaction mixture was stirred at room temperature for 30 minutes and extracted with ethyl acetate. The organic layer was washed with water and saturated aqueous sodium bicarbonate solution, and dried over anhydrous sodium sulfate. The solvent was distilled off, and the resultant crude product was purified by TLC (developing solvent, chloroform:methanol= 9:1) to obtain 5 mg of [6-acetoxy-2-(4-acetoxycyclohexyl)benzo[b]thien-3-yl][ 4-[2-(1-piperidinyl)ethoxy]phenyl]methanone.

¹H-NMR(CDCl₃, δ):1.10~2.20(14H, m), 2.01(3H, s), 2.31(3H, s), 2.60~ 2.90(4H, m), 3.03(2H, t, J=6 Hz), 4.36(2H, t, J=6 Hz), 4.70(1H, m), 6.80~ 7.60(5H, m), 7.80(2H, d, J=8.8 Hz).

MS(m/z):563(M⁺), 452, 434, 393, 351, 309, 98.

The following compound of Example 140 was synthesized in the same manner as in Example 139.

EXAMPLE 140

(6-Acetoxy-2-cyclohexylbenzo[b]thien-3-yl)[4-[2-(1-piperidinyl)ethoxy]phenyl]methanone ¹H-NMR(CDCl₃, δ):1.10~2.20(16H, m), 2.31(3H, s), 2.40~2.70(4H, m), 2.81(2H, t, J=6 Hz), 3.00(1H, m), 4.19(2H, t, J=6 Hz), 6.80~7.60(5H, m), 7.80(2H, d, J=8.8 Hz).

An example of preparation of a drug containing a compound of this invention is shown below.

|  | mg/tablet |
|---|---|
| Active ingredient | 10.0 |
| Starch | 20.0 |
| Lactose | 142.0 |
| Carboxymethylcellulose calcium | 5.0 |
| Talc | 2.0 |
| Magnesium stearate | 1.0 |
|  | 180 mg |

The active ingredient is pulverized into a grain size of 70 microns or less, the starch, lactose and carboxymethylcellulose calcium were added thereto, and the mixture is sufficiently mixed. A 10% starch paste is added to the mixture and the resultant mixture is stirred and mixed to prepare granules. After drying, the granules are graded so that the grain size becomes around 1,000 microns, talc and magnesium stearate are added thereto, and the mixture is tableted.

Industrial Applicability

The compounds of the above formula (I) of this invention have an antiestrogenic activity, and are useful for curing or treatment of estrogen-dependent diseases such as, for example, breast cancer, endometrial cancer, endometriosis, prostatomegaly and mastopathy.

We claim:

1. A benzothiophene derivative represented by the following general formula or a salt thereof

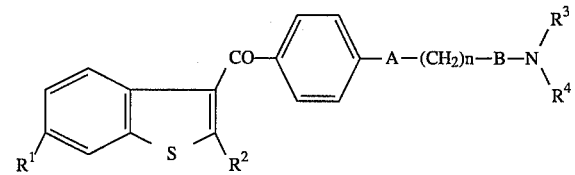

wherein

R¹ denotes a hydroxyl group, a lower alkoxy group, an acyloxy group or an N,N-di-lower alkyl-substituted or unsubstituted carbamoyloxy group, R² denotes a halogen atom; a lower alkyl group; or a cycloalkyl or cycloalkenyl group optionally substituted by a lower alkyl group, a hydroxyl group, an acyloxy group or an oxo group, R³ and R⁴ each denote a hydrogen atom or a lower alkyl group, or R³ and R⁴ combine with the nitrogen atom to which they bind, to denote a heterocyclic ring which may further contain a hetero atom selected from O, S and N, A denotes O or CH₂, B denotes C=O or CH₂, and n denotes 1 or 2.

2. The benzothiophene derivative or the salt thereof according to claim 1 wherein $R^2$ denotes a group of the formula

(wherein $R^5$ and $R^6$ each denote a lower alkyl group) or a cycloalkyl group having 3 to 8 carbon atoms optionally substituted by a lower alkyl group or a hydroxyl group.

3. The benzothiophene derivative or the salt thereof according to claim 2 wherein $R^3$ and $R^4$ each denote a lower alkyl group, or $R^3$ and $R^4$ combine with the nitrogen atom to which they bind to denote a 5- to 7-membered heterocyclic group.

4. The benzothiophene derivative or the salt thereof according to claim 3 wherein $R^1$ denotes a hydroxyl group.

5. The benzothiophene derivative or the salt thereof according to claim 4 wherein A denotes O and B denotes $CH_2$.

6. The benzothiophene derivative or the salt thereof according to claim 5 which is (6-hydroxy-2-cyclohexylbenzo[b]thien-3-yl)[4-[2-(1-pyrrolidinyl)ethoxy]phenyl]methanone, (6-hydroxy-2-cyclohexylbenzo[b]thien-3-yl)[4-[2-(1-piperidinyl)ethoxy]phenyl]methanone, (6-hydroxy-2-cycloheptylbenzo[b]thien-3-yl)[4-[2-(1-pyrrolidinyl)ethoxy]phenyl]methanone, (6-hydroxy-2-cycloheptylbenzo[b]thien-3-yl)[4-[2-(1-piperidinyl)ethoxy]phenyl]methanone, (6-hydroxy-2-isopropylbenzo[b]thien-3-yl)4-[2-(1-pyrrolidinyl)ethoxy]phenyl]methanone or (6-hydroxy-2-isopropylbenzo[b]thien-3-yl)[4-[2-(1-piperidinyl)ethoxy]phenyl]methanone.

7. The benzothiophene derivative or the salt thereof according to claim 4 wherein A denotes $CH_2$.

8. The benzothiophene derivative or the salt thereof according to claim 7 which is (6-hydroxy-2-cyclohexylbenzo[b]thien-3-yl)[4-[3-(1-pyrrolidinyl)propyl]phenyl]methanone, (6-hydroxy-2-cyclohexylbenzo[b]thien-3-yl)[4-[3-(1-piperidinyl)propyl]phenyl]methanone or (6-hydroxy-2-cyclohexylbenzo[b]thien-3-yl)[4-[2-(1-pyrrolidinylcarbonyl)ethyl]phenyl]methanone.

9. The benzothiophene derivative or the salt thereof according to claim 3 wherein $R^1$ denotes a lower alkoxyl group or a lower alkylcarbonyloxy group.

10. The benzothiophene derivative or the salt thereof according to claim 9 which is (6-methoxy-2-cyclohexylbenzo[b]thien-3-yl)[4-[2-(1-piperidinyl)ethoxyl]phenyl]methanone or (6-acetoxy-2-cyclohexylbenzo[b]thien-3-yl)[4-[2-(1-piperidinyl)ethoxy]phenyl]methanone.

11. An antiestrogenic agent containing a benzothiophene derivative according to claim 1 or a salt thereof.

* * * * *